US010361382B2

(12) United States Patent
Che

(10) Patent No.: US 10,361,382 B2
(45) Date of Patent: Jul. 23, 2019

(54) PLATINUM COMPLEXES FOR BLUE OLED APPLICATION

(71) Applicant: THE UNIVERSITY OF HONG KONG, Hong Kong (CN)

(72) Inventor: Chi Ming Che, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 345 days.

(21) Appl. No.: 15/405,001

(22) Filed: Jan. 12, 2017

(65) Prior Publication Data

US 2017/0207389 A1 Jul. 20, 2017

Related U.S. Application Data

(60) Provisional application No. 62/279,042, filed on Jan. 15, 2016.

(51) Int. Cl.
| | | |
|---|---|---|
| H01L 51/50 | (2006.01) |
| H01L 51/00 | (2006.01) |
| C09K 11/06 | (2006.01) |
| C09K 11/02 | (2006.01) |
| C07F 15/00 | (2006.01) |

(52) U.S. Cl.
CPC ........ *H01L 51/009* (2013.01); *C07F 15/0086* (2013.01); *C09K 11/025* (2013.01); *C09K 11/06* (2013.01); *H01L 51/008* (2013.01); *H01L 51/0087* (2013.01); *C09K 2211/1007* (2013.01); *C09K 2211/1044* (2013.01); *C09K 2211/185* (2013.01); *H01L 51/5016* (2013.01)

(58) Field of Classification Search
None
See application file for complete search history.

(56) References Cited

PUBLICATIONS

Lin et al., Photofunctional Platinum Complexes Featuring N-heterocyclic Carbene-Based Pincer Ligands, 2015, Chemistry Asian Journal, vol. 10, 728-739 (Year: 2015).*
Che, Chi-Ming, et al. "Photophysical properties and OLED applications of phosphorescent platinum (II) Schiff base complexes." Chemistry-A European Journal 16.1 (2010): 233-247.
Vezzu, Dileep AK, et al. "Highly luminescent tetradentate bis-cyclometalated platinum complexes: design, synthesis, structure, photophysics, and electroluminescence application." Inorganic chemistry 49.11 (2010): 5107-5119.
Zhao, Xiang-Hua, et al. "A 3-dimensional spiro-functionalized platinum (ii) complex to suppress intermolecular #—#and Pt . . . Pt supramolecular interactions for a high-performance electrophosphorescent device." Chemical communications 48.32 (2012): 3854-3856.
Kui, Steven CF, et al. "Robust phosphorescent platinum (II) complexes with tetradentate O/\ N/\ C/\ N ligands: high efficiency OLEDs with excellent efficiency stability." Chemical Communications 49.15 (2013): 1497-1499.

(Continued)

*Primary Examiner* — Gregory D Clark
(74) *Attorney, Agent, or Firm* — Leason Ellis LLP

(57) ABSTRACT

Described herein are compounds that are platinum emitters and, more particularly compounds that are platinum emitters of blue light and their applications in blue emitting organic light-emitting diodes (OLED). Also disclosed herein are devices that comprise the platinum emitters and methods of making and using the platinum emitters.

30 Claims, 16 Drawing Sheets

Synthetic route for complex with Structure I

(56) References Cited

PUBLICATIONS

Cheng, Gang, et al. "Structurally robust phosphorescent [Pt(O^N^C^N)] emitters for high performance organic light-emitting devices with power efficiency up to 126 lm W-1 and external quantum efficiency over 20%." Chemical Science 5.12 (2014): 4819-4830.

D'Andrade, B. W., et al. "High efficiency single dopant white electrophosphorescent light emitting diodes." New J. Chem. 2002, 26, 1171-1178.

Bhansali, Unnat S., et al. "High-efficiency turquoise-blue electrophosphorescence from a Pt (II)-pyridyltriazolate complex in a phosphine oxide host." Applied Physics Letters 95.23 (2009): 319.

Qureshi, Zubair A., et al. "Treatment outcome of bacteremia due to KPC-producing Klebsiella pneumoniae: superiority of combination antimicrobial regimens." Antimicrobial agents and chemotherapy 56.4 (2012): 2108-2113.

Fleetham, Tyler, et al. "Single-Doped White Organic Light-Emitting Device with an External Quantum Efficiency Over 20%." Advanced Materials 25.18 (2013): 2573-2576.

Lai, Siu-Wai, et al. "Probing d8—d8 Interactions in Luminescent Mono-and Binuclear Cyclometalated Platinum (II) Complexes of 6-Phenyl-2, 2-bipyridines." Inorganic Chemistry 38.18 (1999): 4046-4055.

Lu, Wei, et al. "Light-emitting tridentate cyclometalated platinum (II) complexes containing σ-alkynyl auxiliaries: tuning of photo- and electrophosphorescence." Journal of the American Chemical Society 126.15 (2004): 4958-4971.

\* cited by examiner

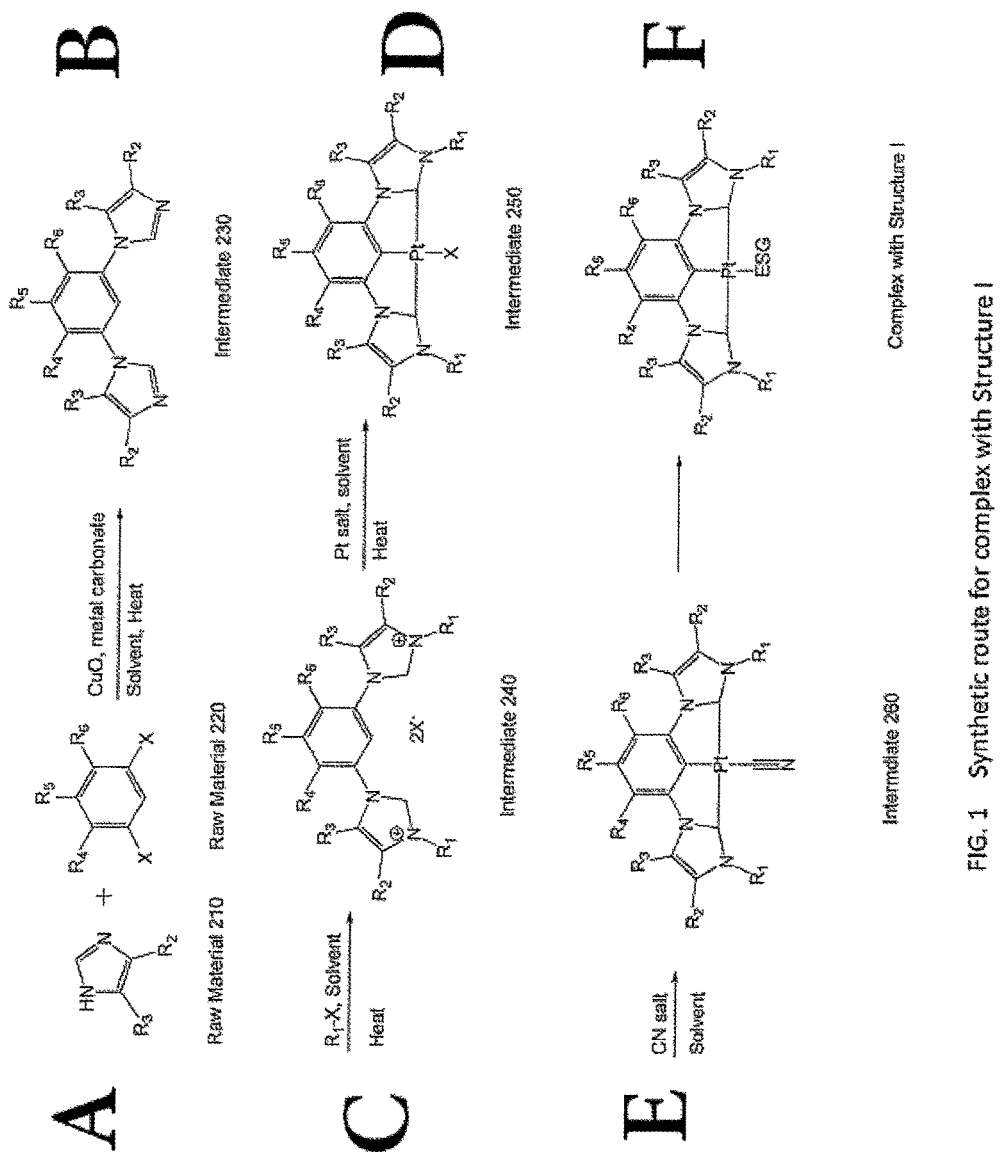
FIG. 1 Synthetic route for complex with Structure I

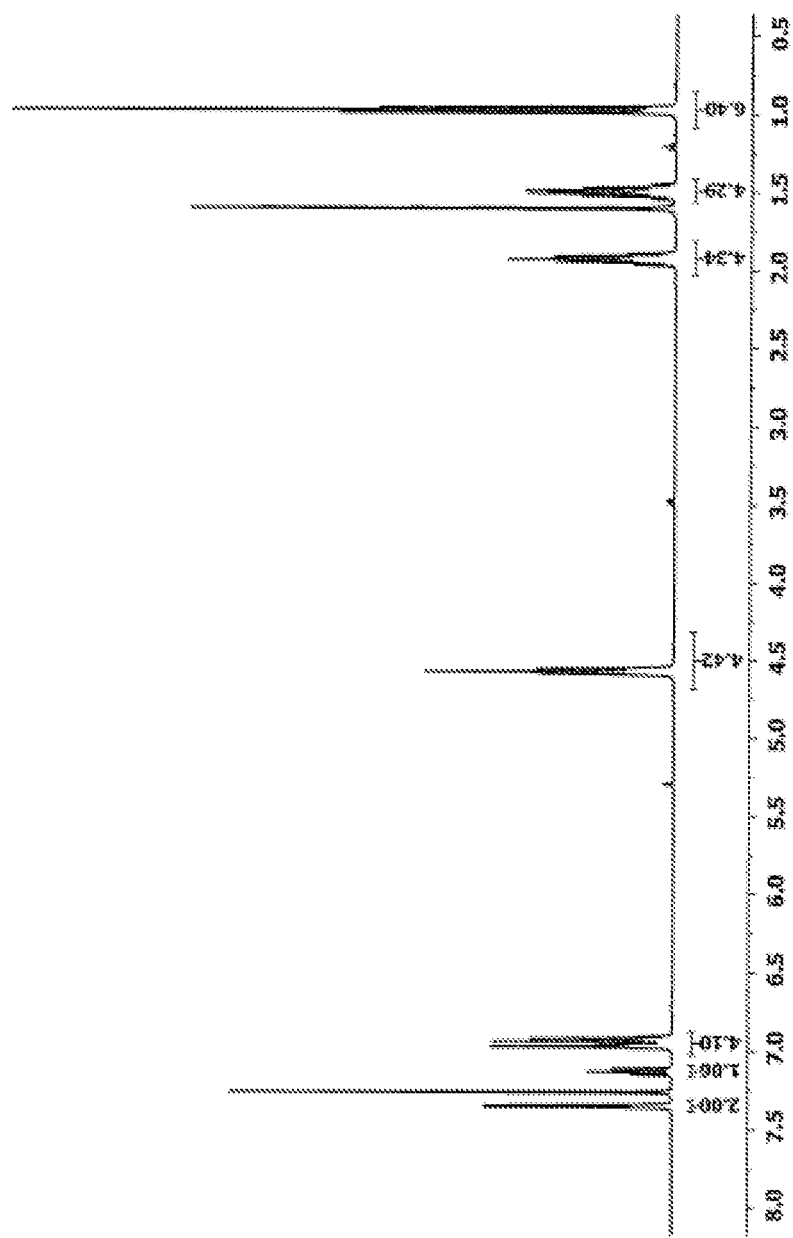
FIG. 2  ¹H NMR spectrum of intermediate 261

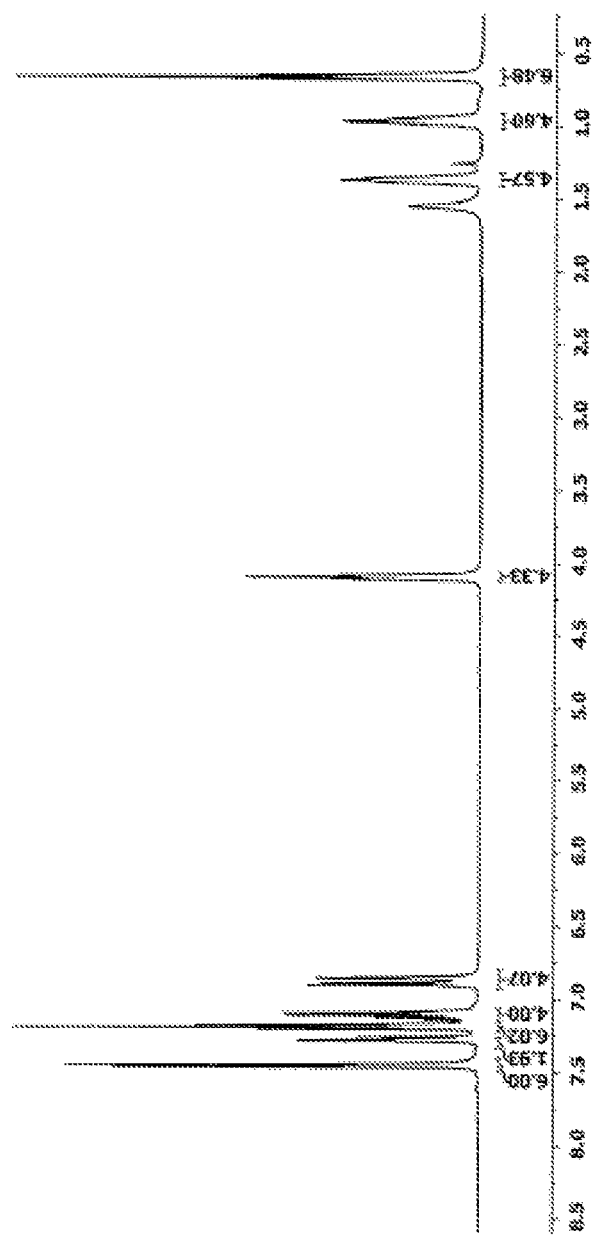

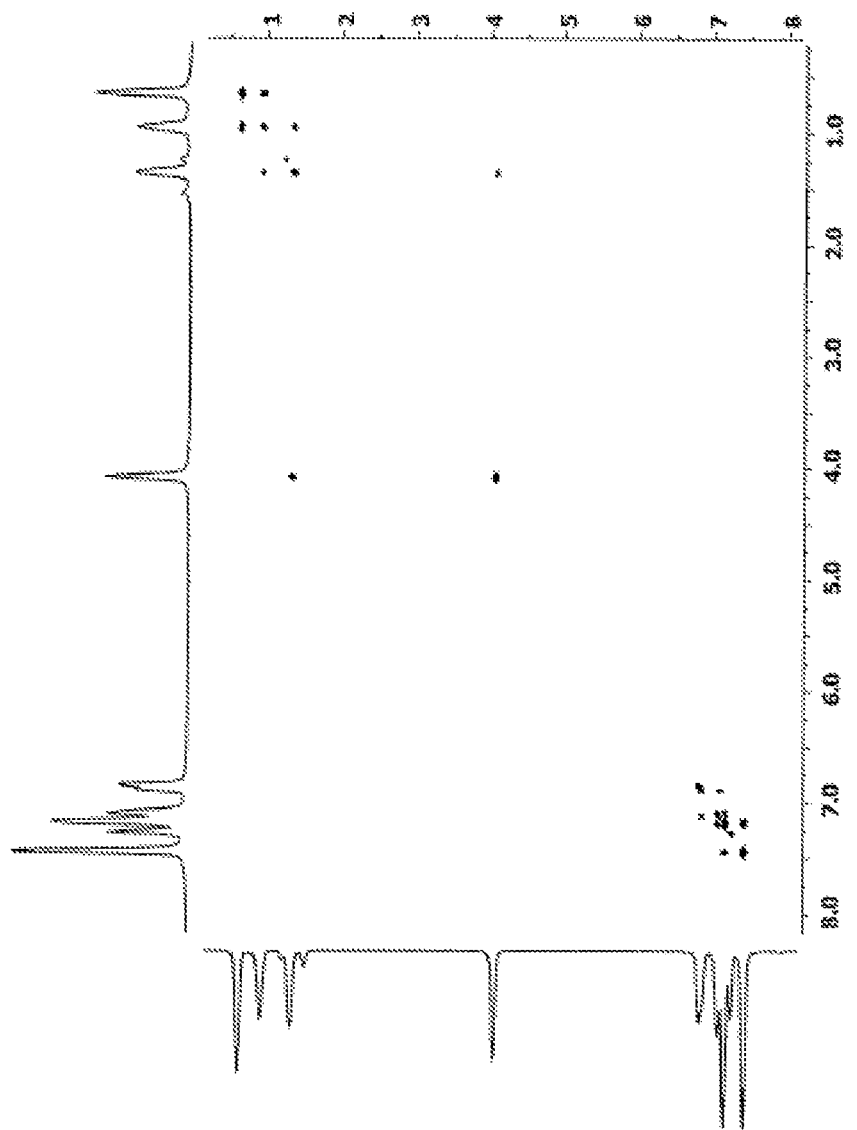
FIG. 4 H-H COSY NMR spectrum of Emitter 1016

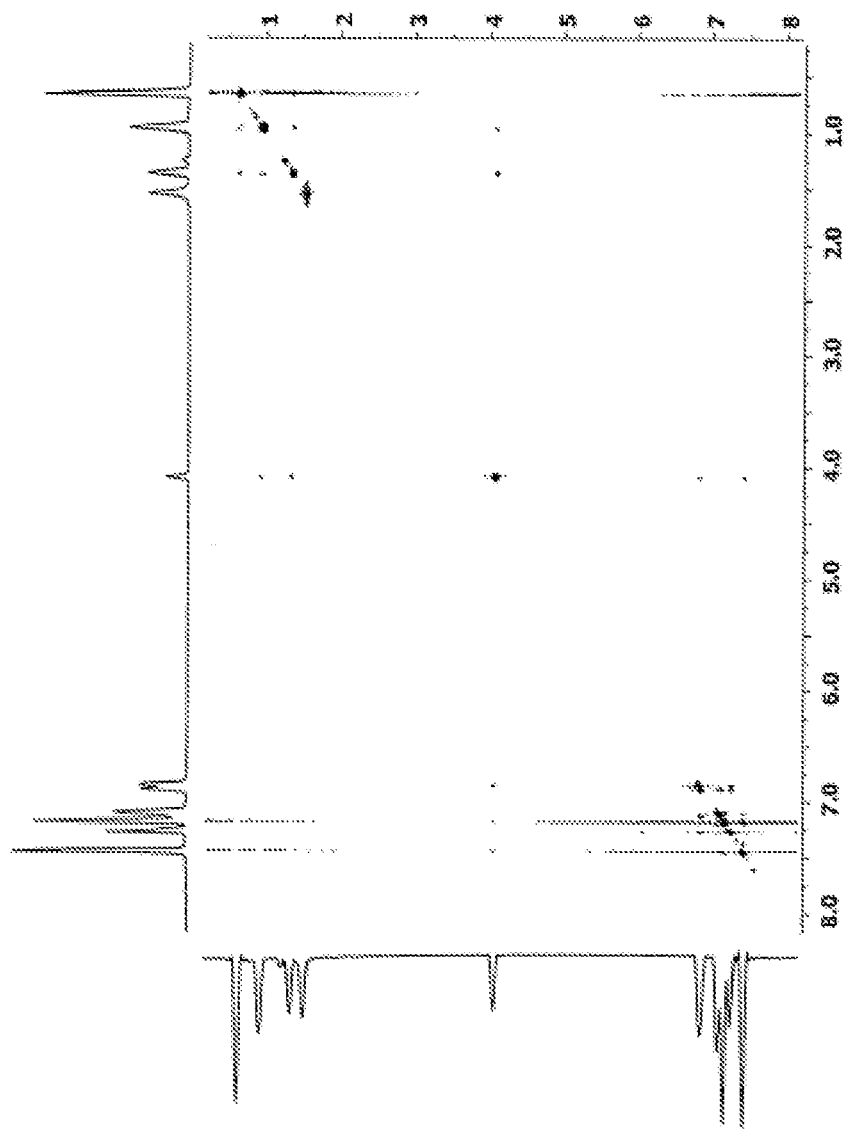
FIG. 5 NOESY-2D NMR spectrum of Emitter 1016

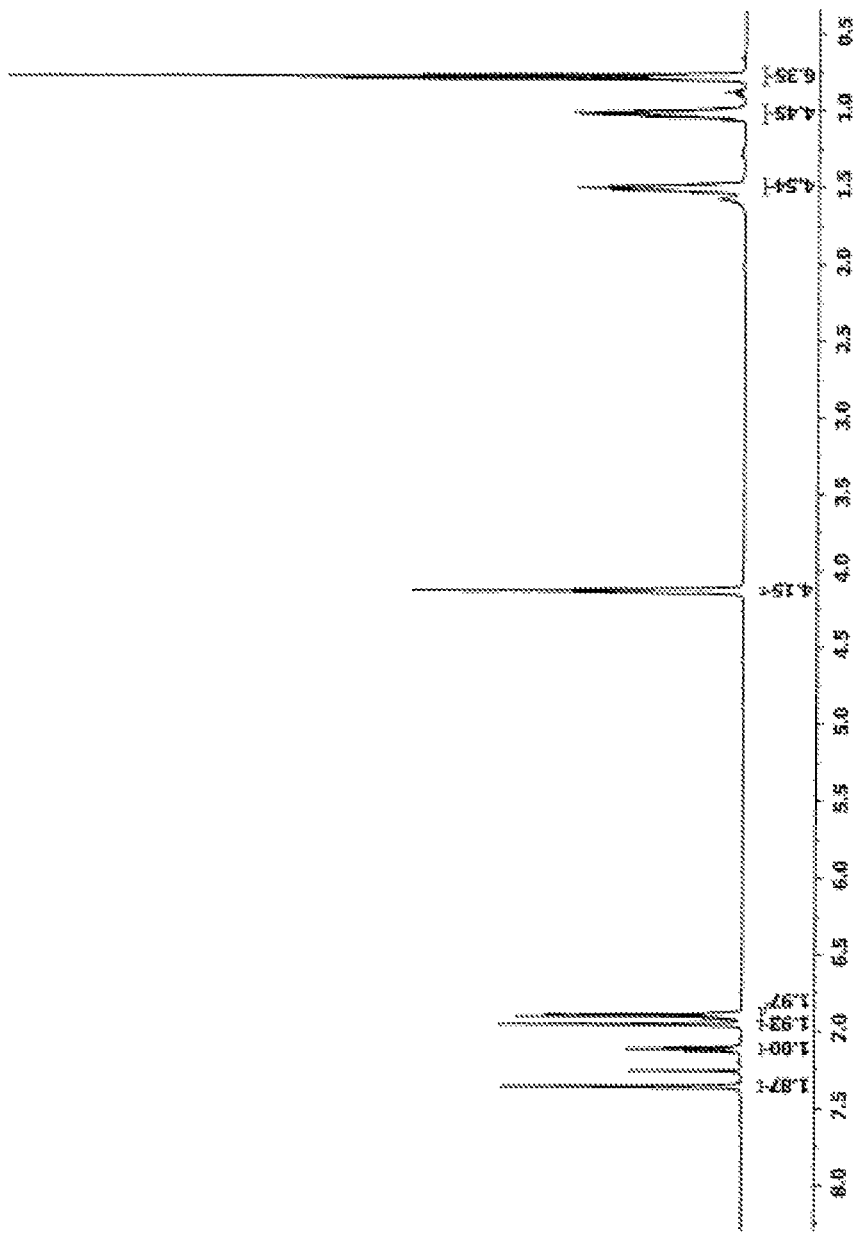
FIG. 6 ¹H NMR spectrum of Emitter 1017

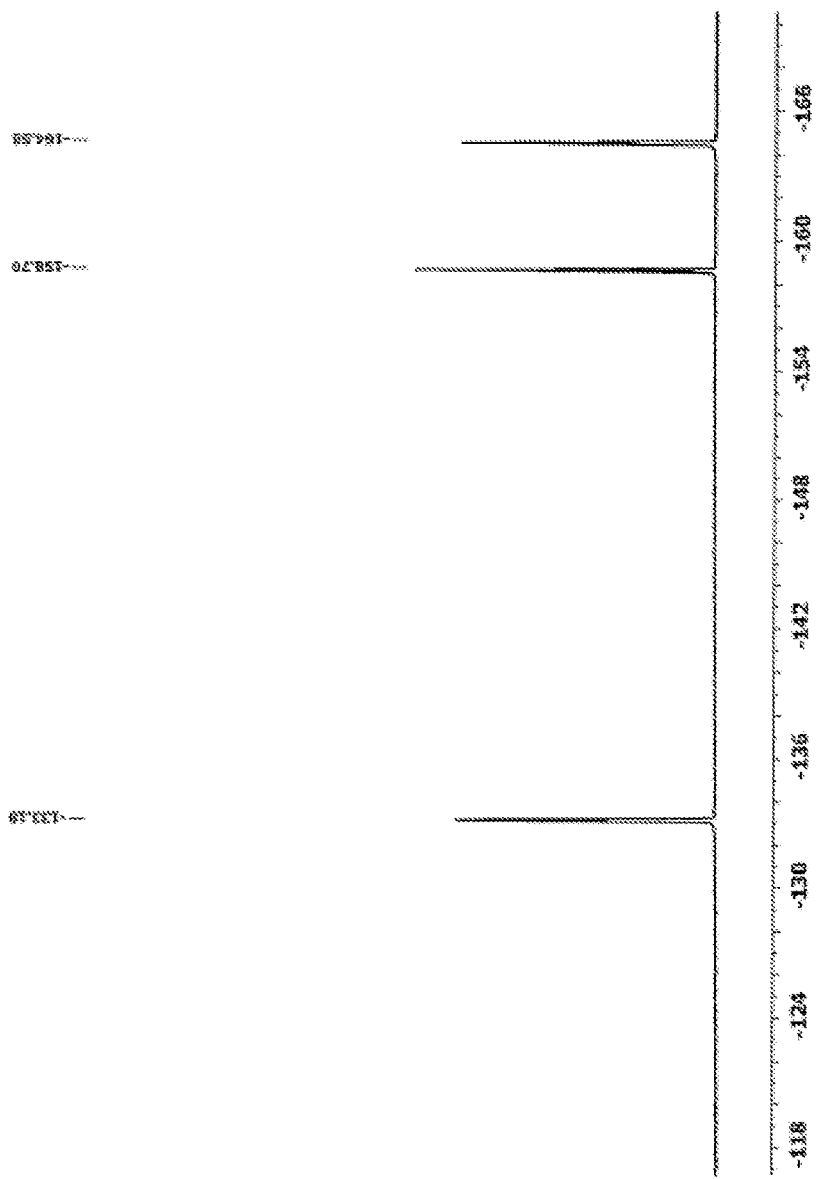
FIG. 7  $^{19}$F NMR spectrum of Emitter 1017

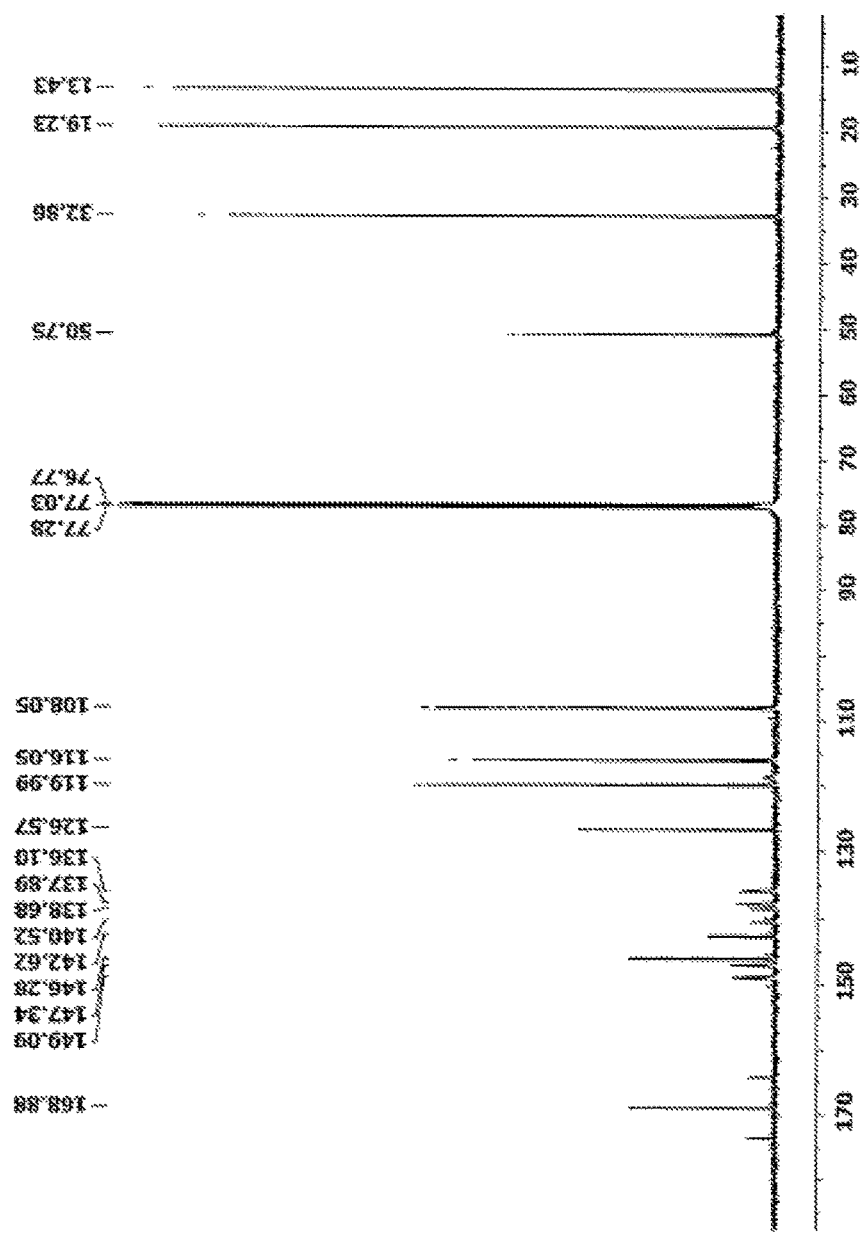
FIG. 8 $^{13}$C NMR spectrum of Emitter 1017

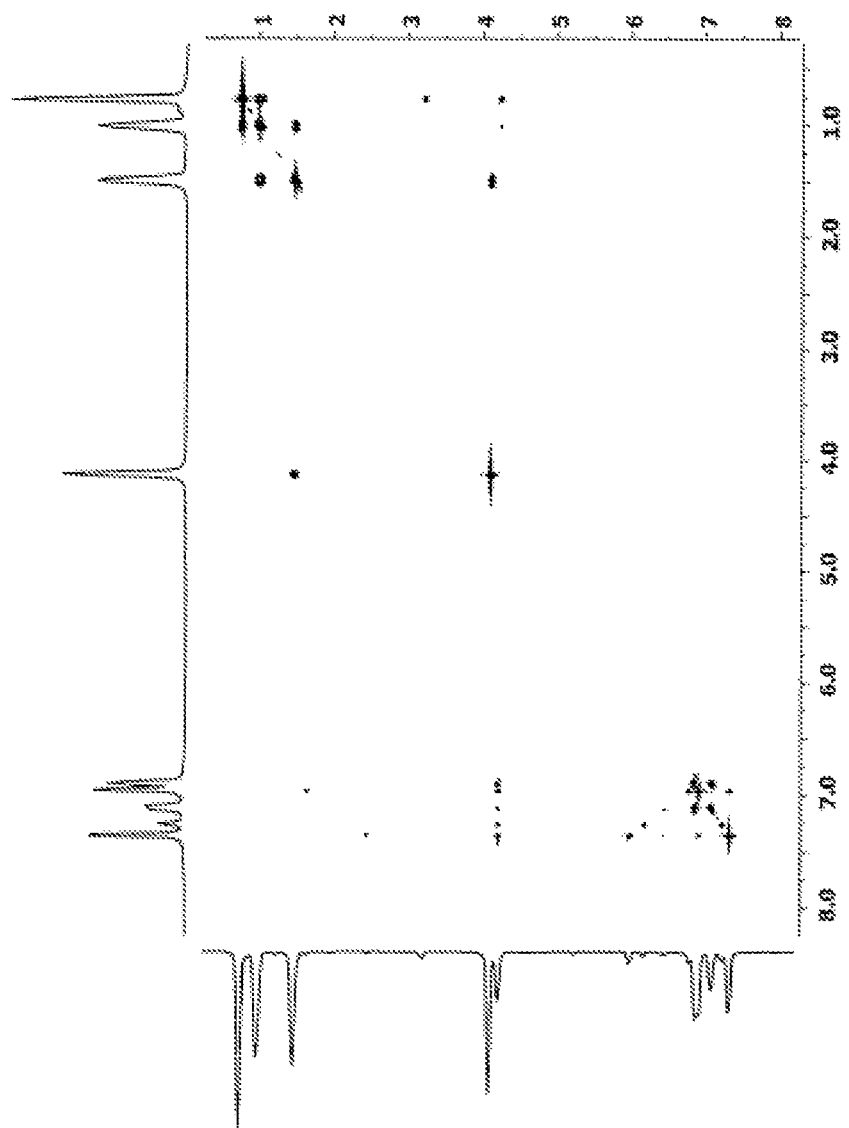
FIG. 9 H-H COSY NMR spectrum of Emitter 1017

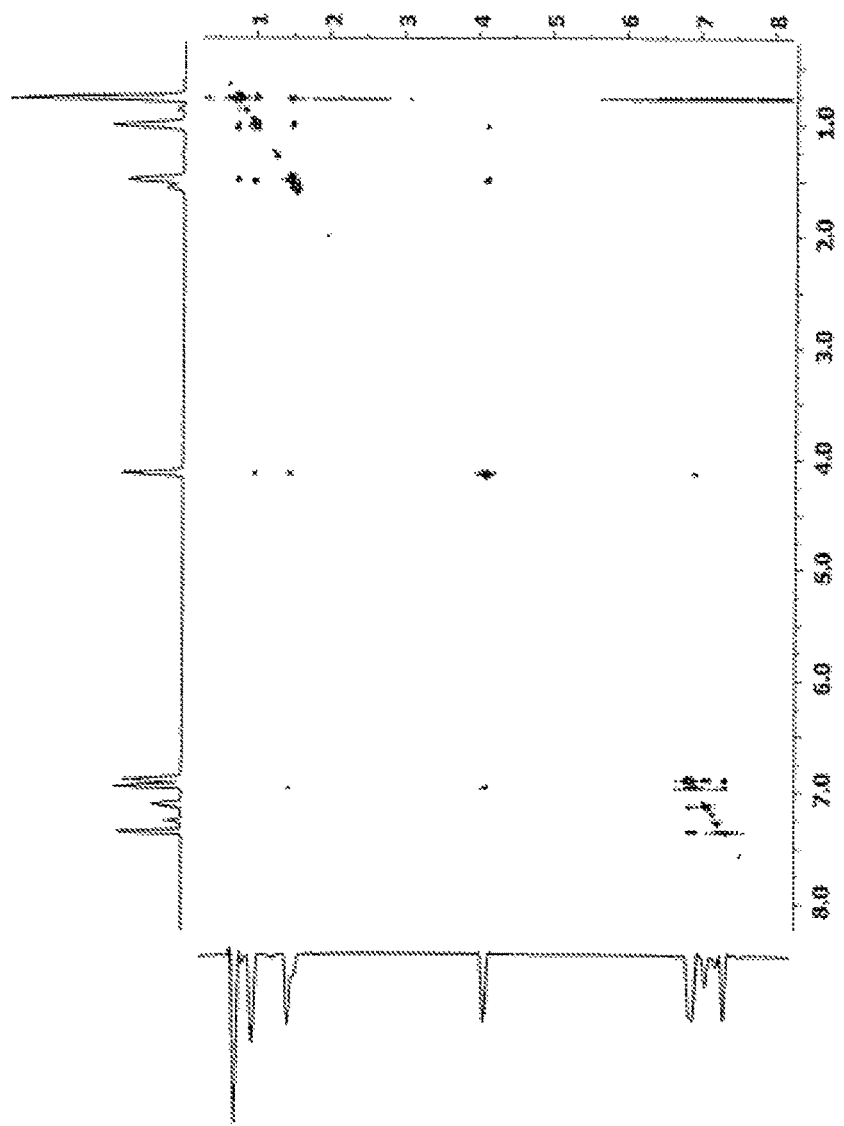
FIG. 10 NOESY-2D NMR spectrum of Emitter 1017

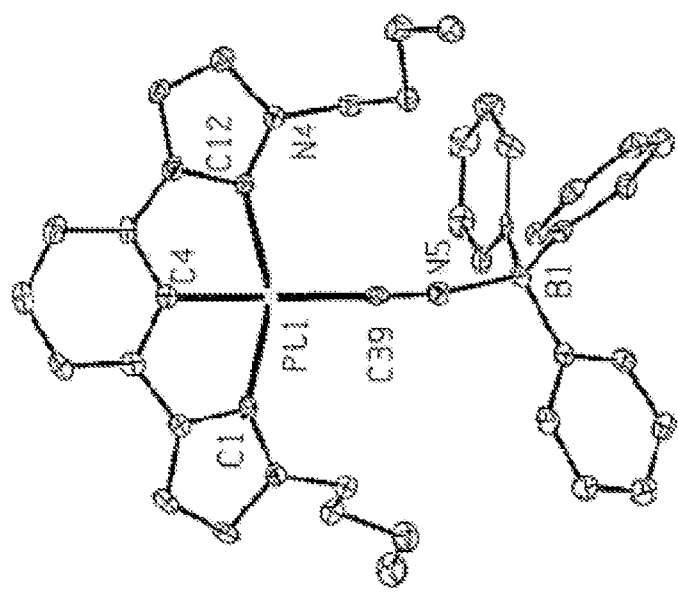
FIG. 11 Perspective view of Emitter 1016

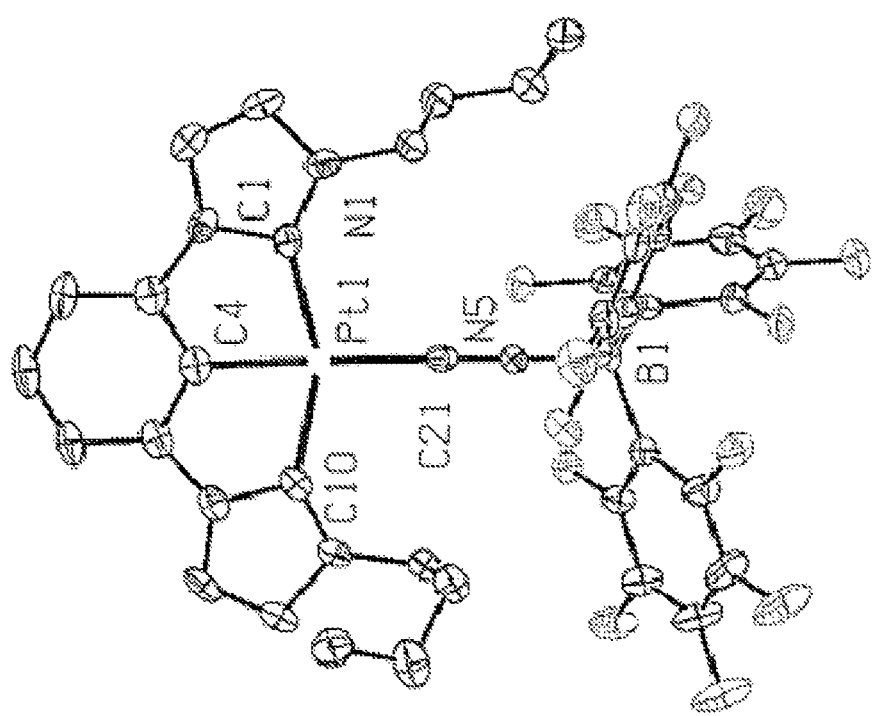
FIG. 12 Perspective view of Emitter 1017

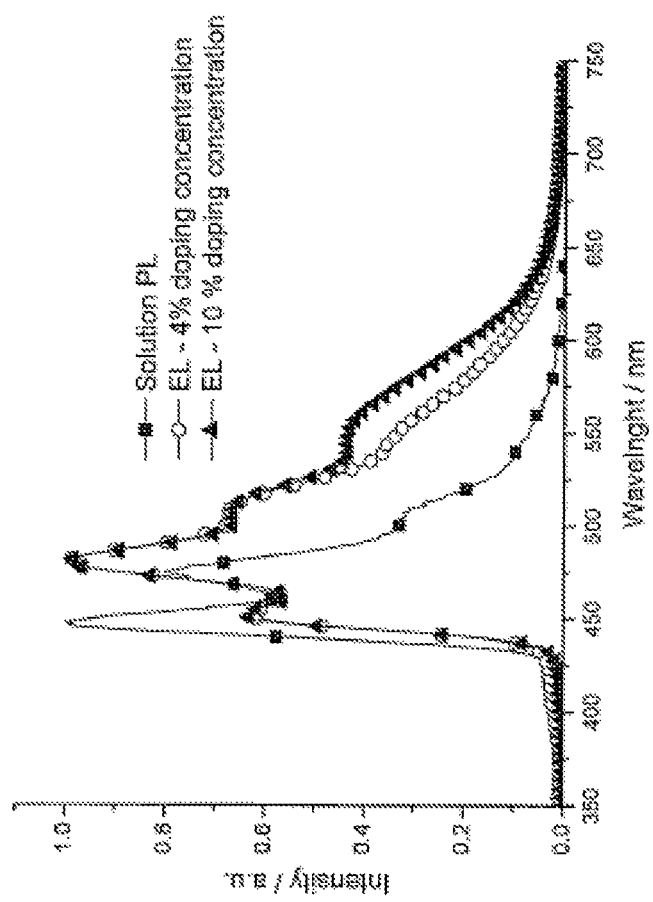
FIG. 13 Solution PL and EL spectra of model complex

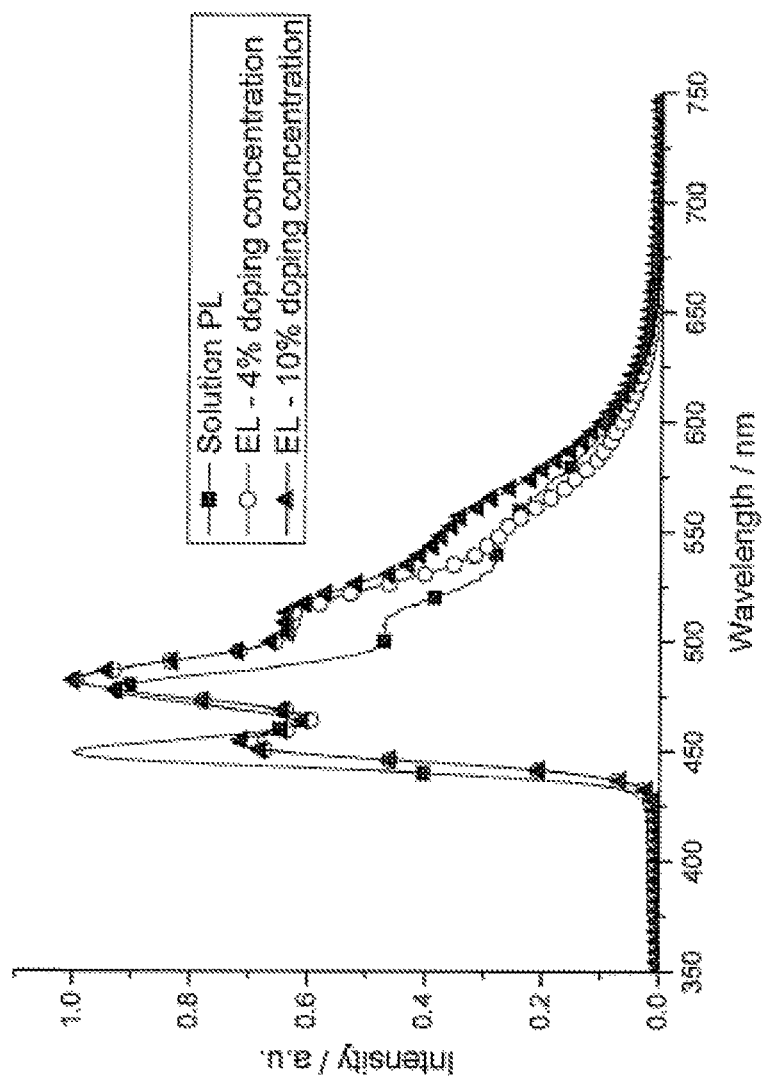
FIG. 14  Solution PL and EL spectra of Emitter 1016

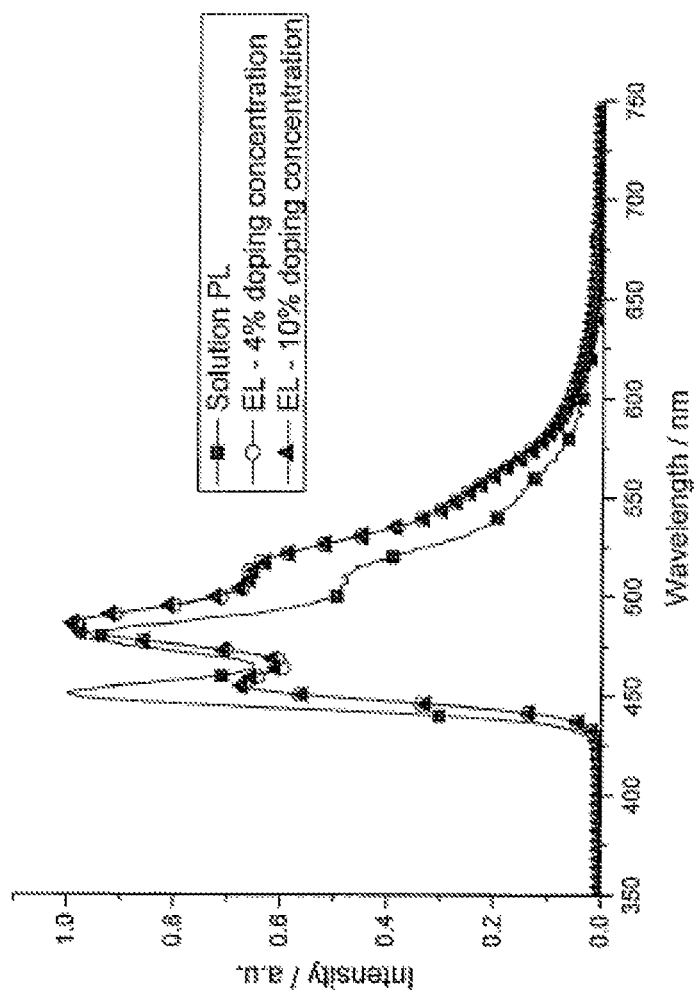
FIG. 15  Solution PL and EL spectra of Emitter 1017

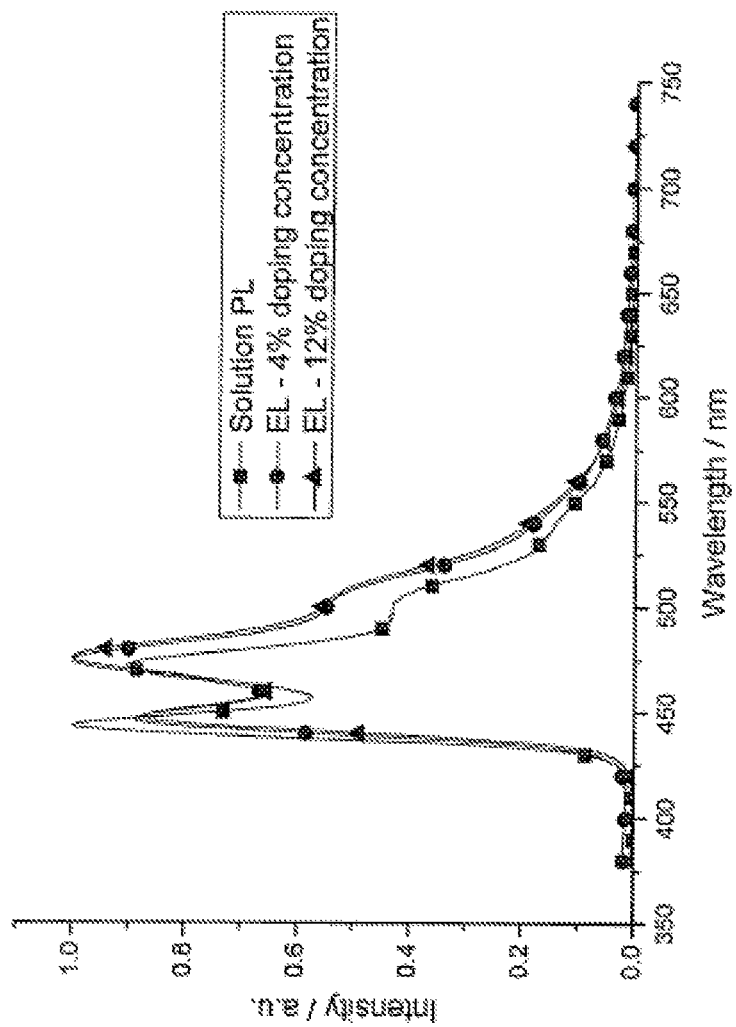
FIG. 16  Solution PL and EL spectra of Emitter 1018

PLATINUM COMPLEXES FOR BLUE OLED APPLICATION

RELATED APPLICATIONS

This application claims the benefit of U.S. provisional application Ser. No. 62/279,042, filed Jan. 15, 2016, which is hereby incorporated by reference in its entirety.

INTRODUCTION

Described herein are compounds that are platinum emitters and, more particularly compounds that are platinum emitters of blue light and their applications in blue emitting organic light-emitting diodes (OLED). Also disclosed herein are devices that comprise the platinum emitters and methods of making and using the platinum emitters.

BACKGROUND

As phosphorescent platinum(II) complexes can be thermally stable and have high emission quantum efficiency, they are potential dopant materials for OLED application. However, due to square planar geometry, platinum(II) complexes have a high self-aggregation tendency, which results in a red-shift in emission $\lambda_{max}$; excimer emission; and low device efficiency.

Considerable effort has been made to deal with this issue; bulky groups such as tert-butyl group(s) and non-planar phenyl group(s) have been added to the platinum(II) complexes. Nevertheless, most of them are not successful. In 2010, Che added tert-butyl group(s) in red-emitting platinum(II) material. [Chem. Eur. J. 2010, 16, 233-247] However, close intermolecular stacking π-π interactions were still observed in the X-Ray crystal structure which means the problem cannot be resolved. In the same year, Huo reported a class of platinum(II) materials containing a non-planar phenyl ring, however excimer emission appears in doping concentration more than 4 wt. % and severe triplet-triplet annihilation was observed even in a device with a mix host, which means this approach cannot resolve the problem [Inorg. Chem. 2010, 49, 5107-5119]. In 2013, Xie prepared new emitters containing two non-planar Spiro-structures. [Chem. Commun. 2012, 48, 3854-3856] However, the devices fabricated by this emitter show serious efficiency roll-off of greater than 50% which indicates adding non-planar group(s) may be able to reduce self-aggregation. In the same year, Che combined the two approaches and used a new, robust (O^N^C^N) ligand system to prepare new platinum(II) materials. In which, one of the emitters shows a wide doping window and slow efficiency roll-off [Chem. Commun. 2013, 49, 1497-1499]. However, the maximum current efficiency of the device can only achieve 66.7 cd/A, even the emission quantum efficiency of the device is 90%. If the self-aggregation effect is resolved, approximately, or even greater than 100 cd/A can be obtained with this emission quantum efficiency. In 2014, Che constructed a new ligand structure containing a Spiro linkage in the ligand which resolved the self-aggregation problem; a green device with power efficiency up to 126 lm/W has been fabricated. [Chem. Sci. 2014, 4819-4830] These examples show that no universal approach can be used in all platinum(II) complexes. A method that works in system A may cause bigger problems in system B.

Furthermore, the systems mentioned above are not suitable for developing blue emitting platinum(II) complexes. Those ligand systems are complicated and have long π-conjugation, such as tetradentate ligands. The emission $\lambda_{max}$ of the complexes developed by these approaches are larger than 500 nm and thus no blue emitter can be prepared.

For blue emitting platinum(II) complexes, Thompson reported a platinum complex which showed blue emission in dilute solution in 2002 [New J. Chem. 2002, 26, 1171-1178]. Due to strong excimer emission, instead of blue OLED, only single emitter white OLED can be fabricated. In 2009, Bhansali developed Pt(ptp)$_2$ which showed blue emission in dilute solution, but because excimers appear at 2.5% dopant concentration, only yellow to orange OLED can be fabricated in a reasonable doping concentration (greater than or equal to 5% by weight) [Appl. Phys. Lett. 2009, 95, 233304]. In 2012, Li reported Pt-16 which was fabricated into blue OLED [Organ. Electron. 2012, 1430-1435]. However, it was later proved that, due to excimer emission, blue emission cannot be maintained using these approaches when the doping concentration was increased to more than 2% by weight, meaning that only white OLED can be obtained. [Adv. Mater. 2013, 25, 2573-2576].

Besides excimer emission, changing the chemical structure of the complexes also results in a red-shift in monomer emission which is not good for blue emitting material development. For example, changing the auxiliary ligand of (tridendate ligand)Pt (auxiliary ligand) type complexes from halide [Inorg. Chem. 1999, 38, 4046-4055] to —C≡C—R [J. Am. Chem. Soc. 2004, 126, 4958-4971] proved largely red-shift emission $\lambda_{max}$ (up to 65 nm red-shift was observed). Therefore, consideration of fixing the excimer emission issue in this way is avoided.

SUMMARY

The compounds and techniques described herein provide an approach to developing blue emitting platinum(II) which minimizes the red-shift in emission $\lambda_{max}$ attributed to excimer emission when an excimer suppression group (ESG) is added. An excimer suppression group is a group whose characteristics are designed to minimize the appearance of, or compensate for, excimer molecule formation in dopant materials for OLED application. In certain embodiments, excimer emission can be completely suppressed in OLED with an ESG. Excimer suppression is valuable in fabricating blue light emitting OLED as blue light emission is particularly sensitive to the increase in wavelength toward the red spectrum caused by excimer emission. Further, with excimer formation being suppressed, blue OLED with dopant concentration larger than 5% can be fabricated and an improved device efficiency can be achieved.

In one aspect, the compounds and techniques described herein include blue platinum(II) emitters for use in OLED that have improved device efficiency and minimized excimer effects.

In one or more embodiments described herein, blue OLED are fabricated with dopant concentration larger than 5%. In one or more embodiments, the emitters described herein implement dopant concentrations of 5-30% by weight. In certain embodiments, the emitters described herein implement dopant concentrations of 5-6%, 6-7%, 7-8%, 8-9%, 9-10%, 10-11%, 11-12%, 12-13%, 13-14%, 14-15%, 15-16%, 16-17%, 17-18%, 18-19%, 19-20%, 20-21%, 21-22%, 22-23%, 23-24%, 24-25%, 25-26%, 26-27%, 27-28%, 28-29%, or 29-30% by weight.

The compounds and techniques herein are directed toward producing blue OLED at emission $\lambda_{max}$ not larger than 500 nm. In certain embodiments, the blue light emitted has a wavelength between 440 nm and 500 nm, 460 nm and 480 nm, 465 nm and 475 nm, or 475 nm. In other embodiments, the blue light emitted has a wavelength between 440-450 nm, 450-460 nm, 460-470 nm, 470-480 nm, 480-490 nm, or 490 nm-500 nm. The blue light emitted can also be measured according to the International Commission on Illumination (CIE) x, y coordinate system. In certain embodiments, the CIE x-coordinate has a value of less than 0.20, less than 0.15, or less than 0.1. In certain embodiments, the CIE y-coordinate has a value of less than 0.35, less than 0.25, less than 0.15, less than 0.1, or less than 0.05.

In one aspect, the platinum(II) emitters described herein minimize red-shift of $\lambda_{max}$. An ESG can be selected to minimize red-shift effects (compared to non-ESG, non-halogen group). In certain embodiments, the selected ESG produces a red-shift of less than or equal to 10 nm, 9 nm, 8 nm, 7 nm, 6 nm, 5 nm, 4 nm, 3 nm, 2 nm, 1 nm, or 0 nm relative to those emitters with a halogen in place of the ESG.

In another aspect, the OLED emitters provided herein produce no excimer emission in an electroluminescence (EL) spectrum. In a further aspect, the OLED emitter produces an emission $\lambda_{max}$ in an EL spectrum that is less than an emission $\lambda_{max}$ produced in a solution photoluminescence (PL) spectrum. In a still further aspect, the OLED emitter produces an EL spectrum having no new emission shoulder as compared to a solution PL spectrum produced by the OLED emitter. An emission shoulder is an emission band resulting from excimer emission. In certain embodiments, the OLED emitter produces an EL spectrum that approximates a solution PL spectrum with no excimer emission.

In another aspect, the OLED emitters provided herein show short monomer emission lifetime. In certain embodiments, the OLED emitter shows a monomer emission lifetime of less than 10 µs, 9 µs 8 µs, 7 µs, 6 µs, 5 µs, 4 µs, 3 µs, 2 µs or 1 µs.

Described herein are novel platinum(II) emitters having the chemical structure of Structure I as in FIG. 1F, and their applications in an organic light-emitting diode (OLED). In one or more embodiments, the platinum(II)-based compounds of Structure I are shown as follows:

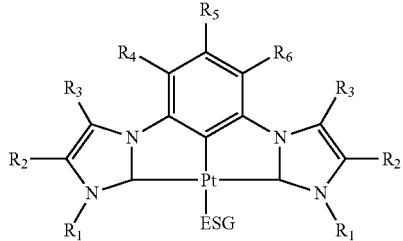

Structure I in which $R_1$-$R_6$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group. Each pair of adjacent R groups of $R_1$-$R_6$ can independently form 5-8 member ring(s) with 2 and/or 4 carbon atoms in the phenyl ring(s) as shown in Structure I. ESG is an excimer suppression group which prevents red-shifting of the monomer emission of the [Pt(II)C(NHC)^C^C(NHC)] emission core and suppresses excimer emission in OLED.

This disclosure also provides devices fabricated from the platinum(II) emitters of Structure I. Advantageously, the devices of the invention exhibit high efficiency. Blue emission can be obtained in this material system as the high energy emission from the [Pt(II)C(NHC)^C^C(NHC)] emission core is maintained and excimer emission is suppressed.

BRIEF DESCRIPTION OF THE DRAWING FIGURES

The invention is illustrated in the figures of the accompanying drawings which are meant to be exemplary and not limiting, in which like references are intended to refer to like or corresponding parts, and in which:

FIGS. 1A-F present a synthetic route for fabricating a complex having chemical structure of Structure I according to one or more embodiments of the present invention;

FIG. 2 presents an exemplary $^1$H NMR spectrum of Intermediate 261 according to one or more embodiments of the present invention;

FIG. 3 presents an exemplary $^1$H NMR spectrum of Emitter 1016 according to one or more embodiments of the present invention;

FIG. 4 presents an exemplary H—H COSY NMR spectrum of Emitter 1016 according to one or more embodiments of the present invention;

FIG. 5 presents an exemplary NOESY-2D NMR spectrum of Emitter 1016 according to one or more embodiments of the present invention;

FIG. 6 presents an exemplary $^1$H NMR spectrum of Emitter 1017 according to one or more embodiments of the present invention;

FIG. 7 presents an exemplary $^{19}$F NMR spectrum of Emitter 1017 according to one or more embodiments of the present invention;

FIG. 8 presents an exemplary $^{13}$C NMR spectrum of Emitter 1017 according to one or more embodiments of the present invention;

FIG. 9 presents an exemplary H—H COSY NMR spectrum of Emitter 1017 according to one or more embodiments of the present invention;

FIG. 10 presents an exemplary NOESY-2D NMR spectrum of Emitter 1017 according to one or more embodiments of the present invention;

FIG. 11 presents a perspective view of Emitter 1016 according to one or more embodiments of the present invention;

FIG. 12 presents a perspective view of Emitter 1017 according to one or more embodiments of the present invention;

FIG. 13 presents a graphical illustration of a solution PL and electroluminescence (EL) spectra of a model complex according to one or more embodiments of the present invention;

FIG. 14 presents a graphical illustration of a solution PL and EL spectra of Emitter 1016 according to one or more embodiments of the present invention;

FIG. 15 presents a graphical illustration of a solution PL and EL spectra of Emitter 1017 according to one or more embodiments of the present invention; and FIG. 16 presents a graphical illustration of a solution PL and EL spectra of Emitter 1018 according to one or more embodiments of the present invention.

DETAILED DESCRIPTION

Definitions

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of an amino group include —NR'R" in which each of R' and R" is independently H, alkyl, aryl, aralkyl, alkaryl, cycloalkyl, acyl, heteroalkyl, heteroaryl or heterocycyl.

"Alkyl" refers to a fully saturated acyclic monovalent radical containing carbon and hydrogen, and which may be branched or a straight chain. Examples of alkyl groups include, but are not limited to, methyl, ethyl, n-propyl, isopropyl, n-butyl, t-butyl, n-heptyl, n-hexyl, n-octyl, and n-decyl.

"Alkylamino" means a radical —NHR or —NR$_2$ where each R is independently an alkyl group. Representative examples of alkylamino groups include, but are not limited to, methylamino, (1-methylethyl)amino, methylamino, dimethylamino, methylethylamino, and di(1-methyethyl)amino.

The term "hydroxyalkyl" means an alkyl radical as defined herein, substituted with one or more, preferably one, two or three hydroxy groups. Representative examples of hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-di hydroxypropyl, 2-hydroxy-1-hydroxymethylethyl, 2,3-dihydroxybutyl, 3,4-dihydroxybutyl and 2-(hydroxymethyl)-3-hydroxy-propyl, preferably 2-hydroxyethyl, 2,3-dihydroxypropyl, and 1-(hydroxymethyl)2-hydroxyethyl. The term "alkoxy," as used herein, refers the radical —OR$_x$. Exemplary alkoxy groups include, but are not limited to, methoxy, ethoxy, and propoxy.

"Aromatic" or "aromatic group" refers to aryl or heteroaryl.

"Aryl" refers to optionally substituted carbocyclic aromatic groups. In some embodiments, the aryl group includes phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Acyl" refers to a monovalent group of the formula —C(=O)H, —C(=O)-alkyl, —C(=O)-aryl, —C(=O)-aralkyl, or —C(=O)-alkaryl.

"Halogen" refers to fluorine, chlorine, bromine and iodine.

"Styryl" refers to a univalent radical C$_6$H$_5$—CH=CH— derived from styrene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl; heteroaryl; hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO$_2$CH$_3$; —CONH$_2$; —OCH$_2$CONH$_2$; —NH$_2$; —SO$_2$NH$_2$; —OCHF$_2$; —CF$_3$; OCF$_3$; —NH(alkyl); —N(alkyl)$_2$; —NH(aryl); —N(alkyl) (aryl); —N(aryl)$_2$; —CHO; —CO(alkyl); —CO(aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

Platinum(II) Emitters

In one aspect, the present invention provides platinum(II) emitters. In one or more embodiments, an organometallic emitter represented by Structure I is provided, as illustrated below. The platinum center in Structure I is in +2 oxidation state and has a square planar geometry. The coordination sites of the platinum center are occupied by a tridentate ligand and an excimer emission suppression group (ESG). The tridentate ligand featuring 5-5 fused membered rings coordinates to the platinum center through a metal-carbon (NHC) bond, a metal-carbon (deprotonated carbon) bond and a metal-carbon (NHC) bond. The ESG is coordinated with the platinum center through a metal-carbon (cyanide) bond.

In one or more embodiments, the platinum(II) emitters have the chemical structures of Structure I:

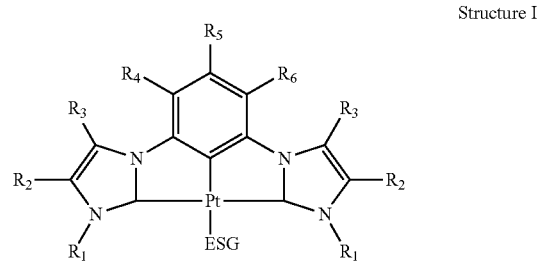

Structure I in which R$_1$-R$_6$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group.

Each pair of adjacent R groups of $R_1$-$R_6$ can be independently form 5-8 member ring(s) with 2 and/or 4 carbon atoms in the phenyl ring(s) showed in Structure I and wherein ESG is an excimer emission suppression group.

In one or more embodiments, the ESG group is

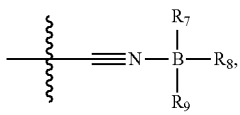

in which $R_7$-$R_9$ are independently an unsubstituted alkyl, a substituted alkyl, cycloalkyl, an unsubstituted aryl, a substituted aryl, acyl, alkoxy, acyloxy or amino group.

In one or more embodiments, $R_1$-$R_6$ is independently hydrogen, halogen, hydroxyl, an unsubstituted alkyl containing from 1 to 20 carbon atoms, a substituted alkyl containing from 1 to 20 carbon atoms, cycloalkyl containing from 4 to 20 carbon atoms, an unsubstituted aryl containing from 6 to 20 carbon atoms, a substituted aryl containing from 6 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thiol, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

In certain embodiments, $R_1$ is $C_4H_9$ or $C_6H_{13}$. In certain embodiments, $R_2$ is H, F, or $CH_3$. In certain embodiments, $R_3$ is H, F or $CH_3$. In certain embodiments, $R_4$ is H, F, or $CH_3$. In certain embodiments, $R_5$ is H, F, $CH_3$, or $CF_3$. In certain embodiments, $R_6$ is H, F, or $CH_3$.

In one or more embodiments, ESG is:

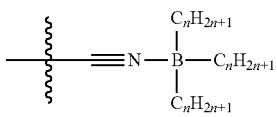

in which n is an integer. In certain embodiments, n is an integer having a value of 1-3, 3-6, 6-8, 8-10, 10-15, or 15-20.

In one or more embodiments, ESG is:

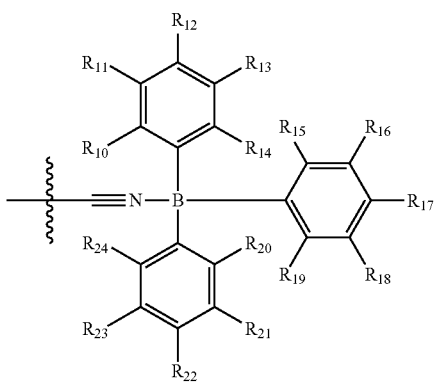

in which $R_{10}$-$R_{24}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group.

In one or more embodiments, ESG is:

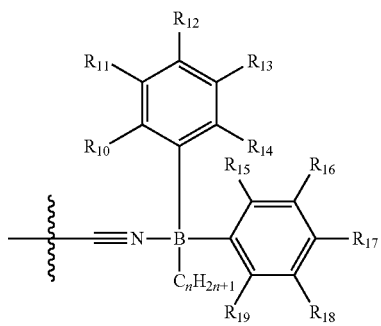

in which $R_{10}$-$R_{19}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group; and n is an integer. In certain embodiments, n is an integer having a value of 1-3, 3-6, 6-8, 8-10, 10-15, or 15-20.

In one or more embodiments, ESG is:

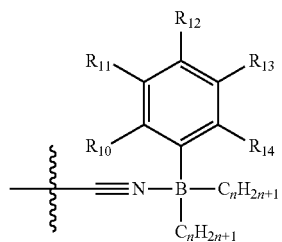

in which $R_{10}$-$R_{14}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group; and n is an integer. In certain embodiments, n is an integer having a value of 1-3, 3-6, 6-8, 8-10, 10-15, or 15-20.

In certain embodiments, the ESG is $B(C_4H_9)_3$, $B(C_6H_{13})_3$, $BPh_3$ or $B(C_6F_5)_3$.

Certain specific, non-limiting examples for the platinum (II) emitters with Structure I are shown as follows:
Emitter 1001
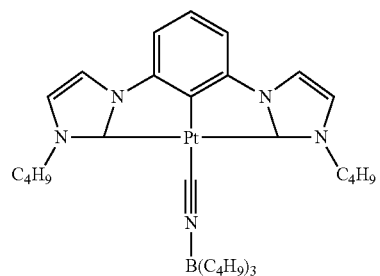
Emitter 1002
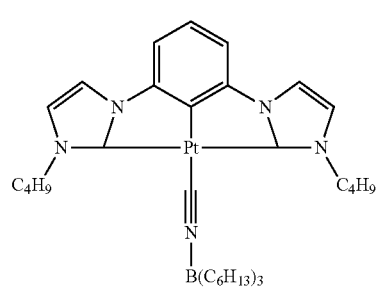
Emitter 1003
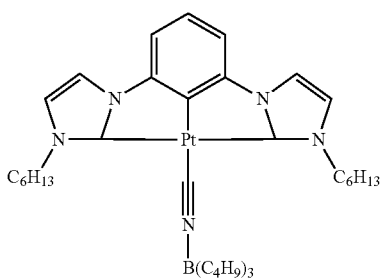
Emitter 1004
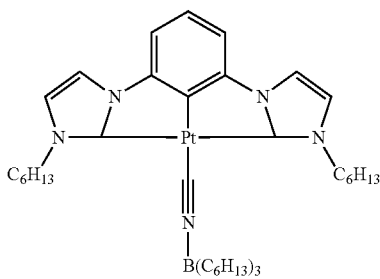
Emitter 1005
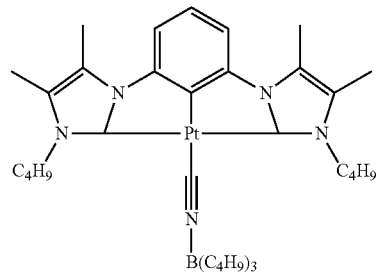
Emitter 1006
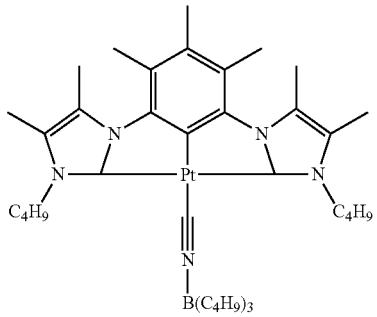
Emitter 1007
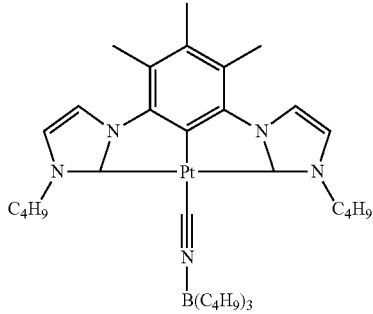
Emitter 1008
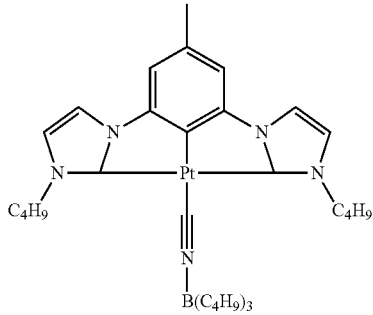
Emitter 1009
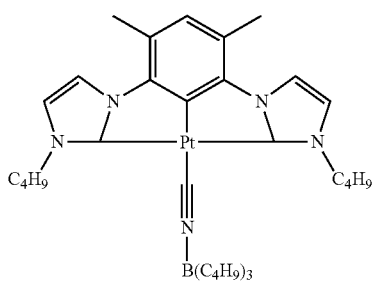
Emitter 1010
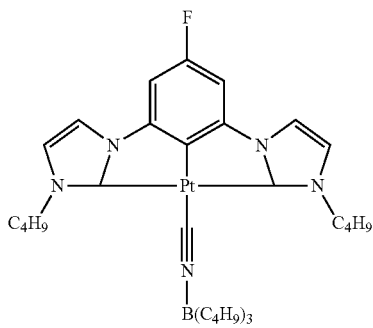

Emitter 1011 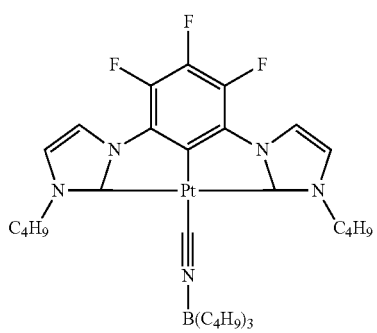

Emitter 1012 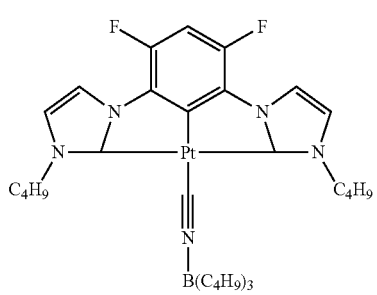

Emitter 1013 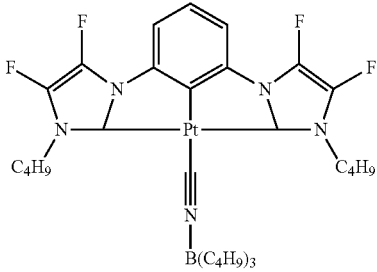

Emitter 1014 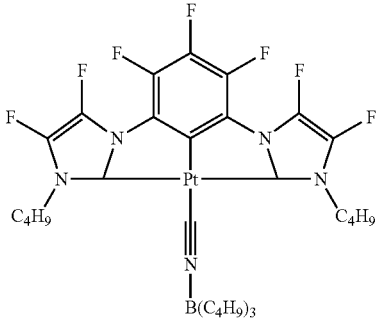

Emitter 1015 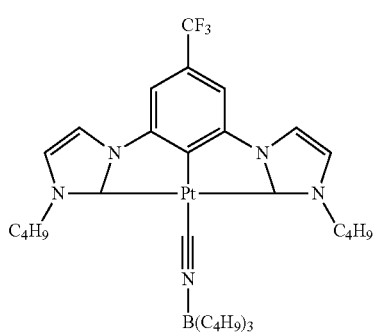

Emitter 1016+ 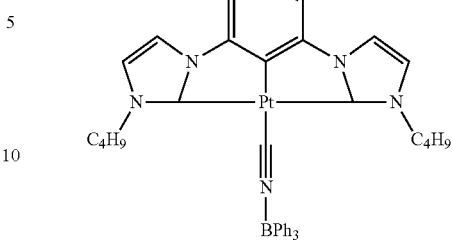

Emitter 1017 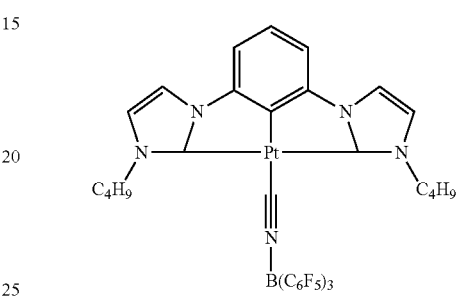

Emitter 1018 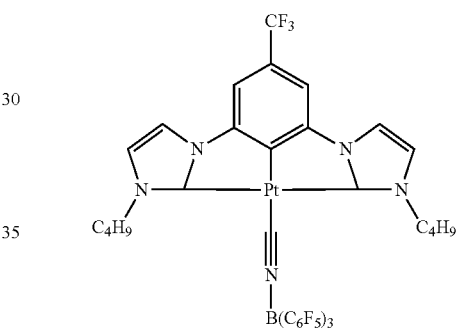

Preparation of Platinum(II) Emitter

In one or more embodiments, the platinum(II) emitter with chemical structure of Structure I can be prepared by a series of reactions depicted in FIGS. 1A-F. In some embodiments, the solvents used in each step are the same. In other embodiments, the solvents used in each step are different. For example, suitable solvents for preparing the platinum(II) emitter having the structure of Structure I include: benzene, chlorobenzene, toluene, dichloromethane (DCM), chloroform, dimethylsulfoxide (DMSO), dimethylformamide (DMF), acetonitrile (ACN), methanol (MeOH), tetrahydrofuran (THF), ethyl acetate (EA), diethyl ether, hexane, pentane, petroleum ether (PE) and acetone.

As shown in FIGS. 1A-B, Raw Material 210 reacts with Raw Material 220 to form Intermediate 230 in the presence of CuO and a metal carbonate in suitable solvent(s). In one or more embodiments, the reaction of Raw Material 210 with Raw Material 220 is performed with the application of heat. In certain embodiments, Raw Material 210 includes substituted and unsubstituted imidazoles. In certain embodiments, Raw Material 220 includes substituted benzenes. For example, Raw Material 220 can include bihalobenzenes and haloalkyl-bihalobenzenes.

As shown in FIG. 1C, Intermediate 230 is then transformed to Intermediate 240 in the presence of $R_1$—X in suitable solvent(s) with the optional application of heat. X is a halogen atom. By reacting Intermediate 240 with platinum salt in suitable solvent(s) with the optional application of heat, Intermediate 250 can be obtained, as shown by FIG. 1D. The halide bonded to the platinum center can be exchanged to cyanide group by reacting with suitable cyanide salt in a suitable solvent, to obtain Intermediate 260, FIG. 1E. Finally, as illustrated by FIG. 1F, a Complex with Structure I can be prepared by reacting Intermediate 260 with a boron containing compound.

In one or more embodiments, one or more of the steps of the process as illustrated by FIGS. 1A-F can be performed with the application of heat. In one or more embodiments, one or more steps are performed at a temperature between 25° C. and 250° C. In certain embodiments, one or more steps are performed at a temperature between 25° C. and 50° C., 50° C. and 75° C., 75° C. and 100° C., 100° C. and 125° C., 125° C. and 150° C., 150° C. and 175° C., 175° C. and 200° C., 200° C. and 225° C., or 225° C. and 250° C.

EXAMPLES

Following are examples that illustrate embodiments for practicing the invention. These examples should not be construed as limiting. All percentages are by weight and all solvent mixture proportions are by volume unless otherwise noted.

Example 301—Synthesis of Intermediate 231

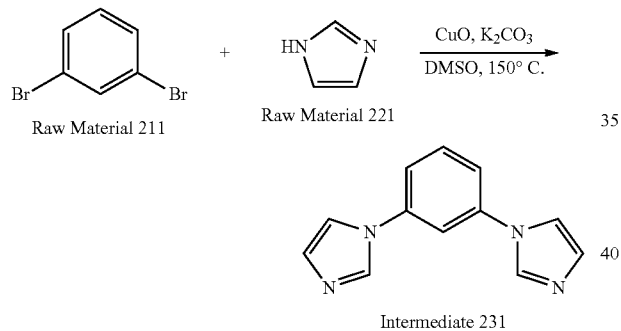

Intermediate 231

Raw Material 211 (2.5 ml, 21 mmol), Raw Material 221 (3.5 g, 52 mmol), $K_2CO_3$ (7.2 g, 52 mmol) and CuO (0.4 g, 5.2 mmol) were mixed and dissolved in DMSO (20 ml). The solution was heated at 150° C. for 48 hours. The reaction was cooled, and the DMSO was distilled at low-pressure, yielding an off-white solid. Chromatography on silica gel (25:1) eluting with $CH_2Cl_2$/MeOH (10:1) gave a white solid (3.3 g, 77%) $^1$H NMR (400 MHz, CDCl$_3$): δ=7.91 (s, 2H), 7.60 (t, J=8.0 Hz, 2H), 7.36-7.47 (m, 3H), 7.32 (s, 2H), 7.23 (s, 2H).

Example 302—Synthesis of Intermediate 232

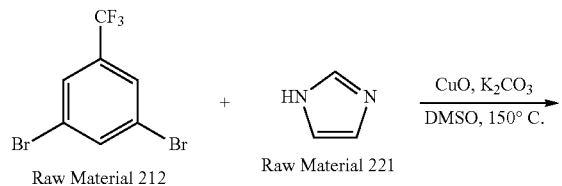

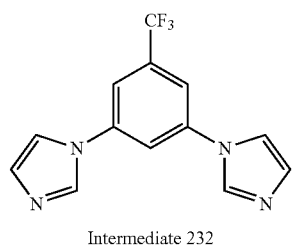

Intermediate 232

Raw Material 212 (1.50 ml, 9.62 mmol), Raw Material 221 (1.64 g, 24 mmol), CuO (0.23 g, 2.89 mmol), potassium carbonate (3.34 g, 24 mmol), and DMSO (20 ml) were mixed and stirred at 150° C. for two days. The reaction was cooled to room temperature and dichloromethane (150 ml) was added. The mixture was filtered through basic activated alumina, and the filter was washed with DCM/MeOH (20 ml/2 ml), giving an amber solution, which was concentrated to dryness to afford a beige residue. Cold ethyl acetate was added and a white solid was obtained. $^1$H NMR (400 MHz, CDCl$_3$): δ=7.96 (s, 2H), 7.65 (s, 2H), 7.63 (s, 1H), 7.37 (s, 2H), 7.29 (s, 2H).

Example 303—Synthesis of Intermediate 241

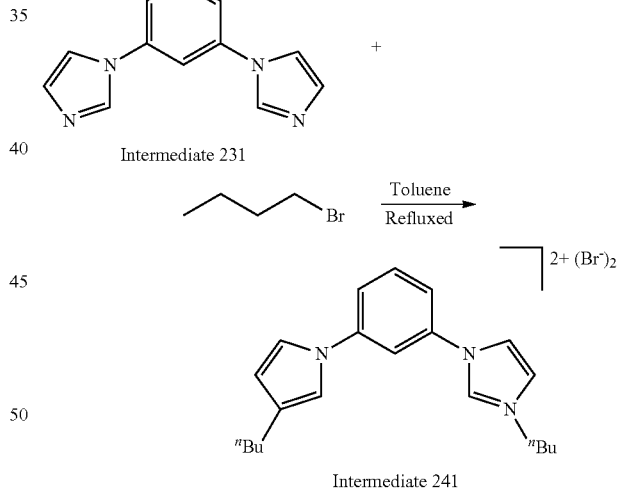

Intermediate 241

The suspension of Intermediate 231 (4.3 g, 20.5 mmol) and 1-bromobutane (8.4 g, 61.3 mmol) in toluene was refluxed at 150° C. for 48 hours. The solid stuck to the bottom of the flask. Solvent was poured out and the solid was washed by THF in order to wash out the viscous elements. The result was to obtain a white solid. Yield: 9.5 g, 18 mmol; 88%. $^1$H NMR (400 MHz, CD$_3$CN): δ=10.84 (s, 2H), 8.79 (s, 1H), 8.36 (d, 2H), 7.94 (d, J=7.68 Hz, 2H), 7.84 (t, J=7.20 Hz, 1H), 7.65 (s, 2H), 4.31 (t, J=7.20 Hz, 2H), 1.99 (quint, J=7.52 Hz, 4H), 1.40 (next, J=7.56 Hz, 4H), 0.98 (t, J=7.28 Hz, 6H).

Example 304—Synthesis of Intermediate 242

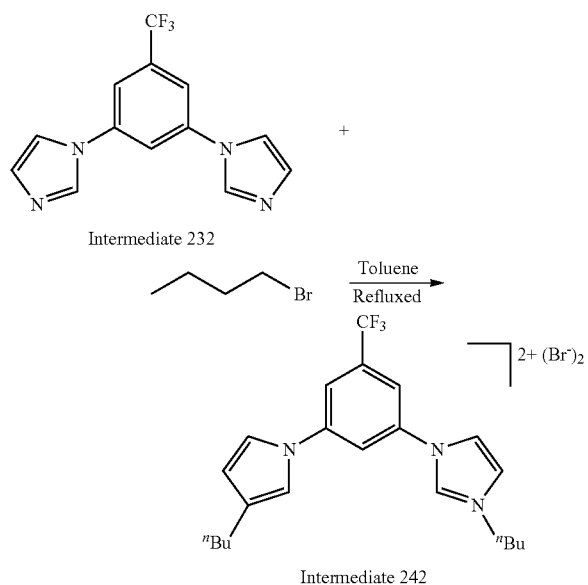

The suspension of Intermediate 232 (1.5 g, 5.4 mmol) and 1-bromobutane (2.94 g, 21.4 mmol) in acetonitrile was refluxed at 150° C. for 48 hours. The yellow solution was filtered through Celite and concentrated. Diethyl ether was added into concentrated acetonitrile solution and a white solid was obtained. Yield: 2.7 g, 4.9 mmol; 90.6%. $^1$H NMR (400 MHz, CD$_3$CN): δ=10.94 (s, 2H), 9.14 (s, 1H), 8.43 (s, 2H), 8.26 (s, 2H), 7.67 (s, 2H), 4.32 (t, J=7.24 Hz, 4H), 1.94 (quint, J=7.44 Hz, 4H), 1.47 (sext, J=7.48 Hz, 4H), 0.98 (t, J=7.36 Hz, 6H).

Example 305—Synthesis of Intermediate 251

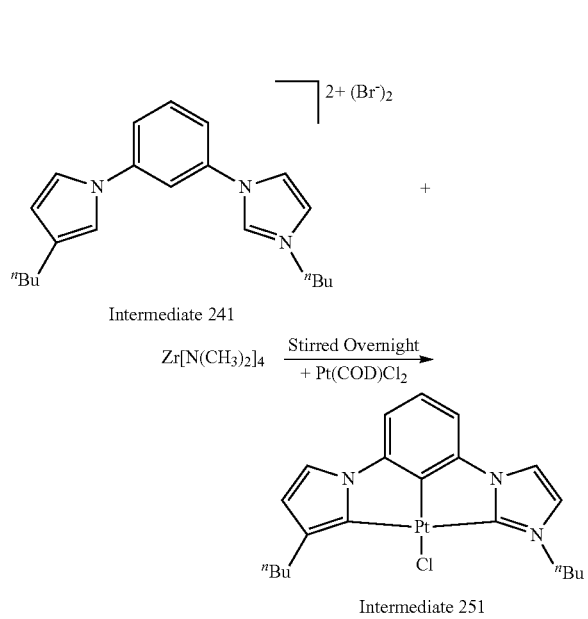

Intermediate 241 (200 mg, 0.4 mmol), tetrakis(dimethylamino)zirconium (200 mg, 1.5 mmol) and CH$_2$Cl$_2$(~5.0 ml) were combined. The mixture was stirred for 1 hour at room temperature to give a red solution. Pt(COD)Cl$_2$ (155 mg, 0.4 mmol) was added, and the mixture was stirred at room temperature overnight. The mixture was permitted to settle. Yellow solid was observed at the bottom of the flask. The red solution was removed and the yellow solid was dissolved in 50 ml dichloromethane and filtered through Celite. The filtration was concentrated and precipitated by adding diethyl ether. Yield: 100 mg, 0.18 mmol; 45%. $^1$H NMR (400 MHz, CDCl$_3$): δ=7.34 (d, 2H), 7.12 (t, J=8.04 Hz, 1H), 6.97 (d, 2H), 6.88 (d, J=7.88 Hz, 2H), 4.72 (t, J=7.24 Hz), 1.89 (quint, J=7.4 Hz, 4H), 1.47 (sext, J=7.72 Hz, 4H), 0.96 (t, J=7.32 Hz, 6H).

Example 306—Synthesis of Intermediate 252

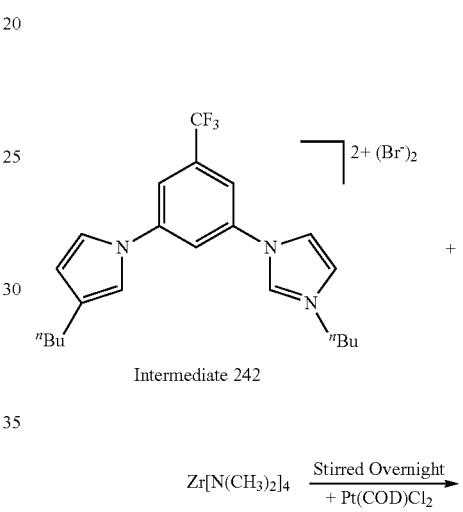

Intermediate 242, tetrakis(dimethylamino)zirconium and CH$_2$Cl$_2$ were combined. The mixture was stirred for 1 hour at room temperature to give a red solution. Pt(COD)Cl$_2$ was added, and the mixture was stirred at room temperature overnight. The mixture was permitted to settle. A solid was observed at the bottom of the flask. The solution was removed and the solid was dissolved in dichloromethane and filtered through Celite. The filtration was concentrated and precipitated by adding diethyl ether. $^1$H NMR (400 MHz, CDCl$_3$): δ=7.41 (s, 2H), 7.13 (t, J=8.32 Hz, 2H), 7.03 (s, 2H), 4.80 (t, J=7.36 Hz, 4H), 1.90 (quint, J=7.48 Hz, 4H), 1.43-1.53 (m, 4H), 0.97 (t, J=7.36 Hz, 6H).

Example 307—Synthesis of Intermediate 261

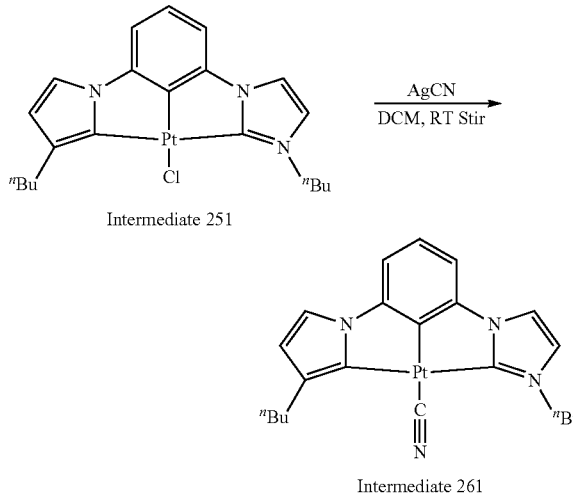

The mixture of Intermediate 251 (100 mg, 0.16 7 mmol) and silver cyanide (24.7 mg, 0.184 mmol) was stirred overnight in dichloromethane. AgBr was removed through Celite, and the filtrate was collected. After removing the solvent by vacuum, a greenish yellow solid was obtained, which yielded 60 mg, 66%. 1H NMR (400 MHz, CDCl$_3$): δ 7.36 (d, 2H), 7.15 (t, 1H), 7.13-6.91 (m, 4H), 4.59 (t, 4H), 1.93 (m, 4H), 1.52 (m, 4H), 0.97 (t, 6H). The $^1$H NMR spectrum of Intermediate 261 is illustrated as FIG. 2.

Example 308—Synthesis of Emitter 1016

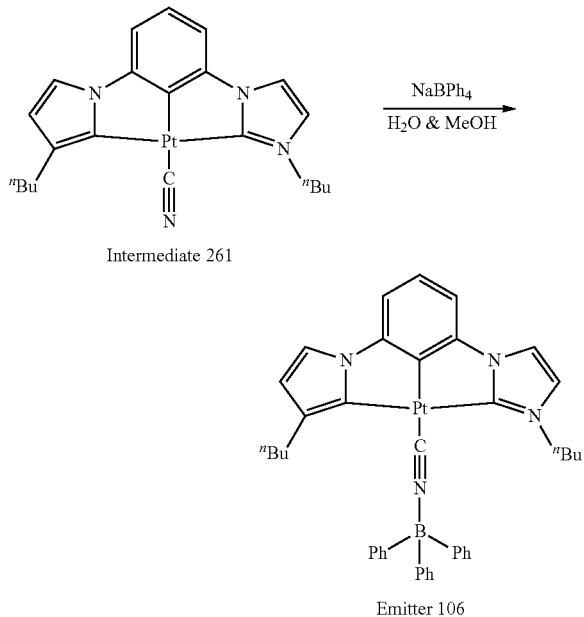

2 ml of hydrochloric acid (3.0 M) was added in a dropwise manner to a stirred suspension of Intermediate 261 (50 mg, 0.092 mmol) in 20 ml mixed solvent of water and methanol (1:1). After 30 minutes, NaBPh$_4$ (65 mg, 0.190 mmol) was added. The resulting solution was stirred overnight at room temperature, during which a light yellow solid gradually precipitated. The precipitate was then collected by filtration and washed with water and methanol. Further purification was achieved by recrystallization from the slow diffusion of diethyl ether into concentrated dichloromethane solution of the complexes. This produced a yield of 60 mg, 0.076 mmol; 82%. $^1$H NMR (500 MHz, CDCl$_3$): δ=7.45 (d, J=6.8 Hz, 6H), 7.32 (s, 2H), 7.18 (t, J=7.4 Hz, 6H), 7.14-7.08 (m, 4H), 6.93-6.79 (m, 4H), 4.09 (t, J=6.2 Hz, 4H), 1.42-1.31 (m, 4H), 0.97 (sext, J=7.3 Hz, 4H), 0.67 (t, J=7.3 Hz, 6H). $^{13}$C {$^1$H} NMR (150 MHz, CDCl$_3$, 25° C., TMS): δ=13.6, 19.1, 32.6, 51.2, 107.8, 115.8, 119.5, 124.2, 126.2, 126.5, 133.9, 140.1, 143.6, 154.1, 169.5 ppm. The $^1$H, H—H COSY and NOESY-2D NMR spectra of Emitter 1016 are illustrated by FIGS. 3-5, respectively.

Example 309—Synthesis of Emitter 1017

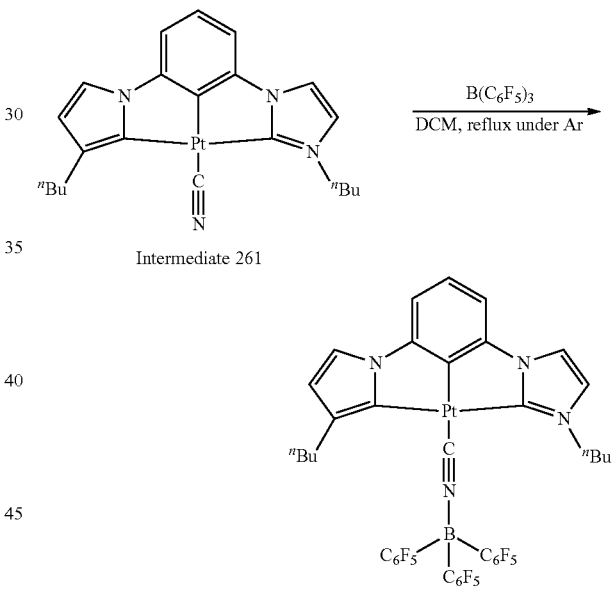

The mixture of Intermediate 261 (58 mg, 0.107 mmol) and B(C$_6$F$_6$)$_3$ (60 mg, 0.117 mmol) was pump-filled three times in a flask. Dry dichloromethane was added into the flask. The solution was stirred overnight at room temperature under argon. A yellow solid was obtained after the solvent was removed by vacuum, which yielded 100 mg, 88.5%. $^1$H NMR (500 MHz, CDCl$_3$): δ 7.36 (s, 2H), 7.12 (t, J=7.8 Hz, 1H), 6.96 (s, 2H), 6.93-6.86 (m, 2H), 4.13 (t, J=6.6 Hz, 4H), 1.55-1.45 (m, 4H), 1.02 (sext, J=7.6 Hz, 4H), 0.79 (t, J=7.3 Hz, 6H). $^{13}$C {$^1$H} NMR (126 MHz, CDCl$_3$, 25° C., TMS): δ=13.4, 19.2, 32.8, 50.8, 108.0, 116.1, 119.9, 120.0, 126.7, 137.0 (d, $^1$J$_{CF}$=260 Hz), 139.63 (d, $^1$J$_{CF}$=250 Hz), 148.06 (d, $^1$J$_{CF}$=242 Hz), 142.8, 146.2, 146.3, 169.0 ppm. The $^1$H, $^{13}$C, $^{19}$F, H—H COSY and NOESY-2D NMR spectra are illustrated by FIGS. 6-10, respectively.

Example 310—Synthesis of Emitter 1018

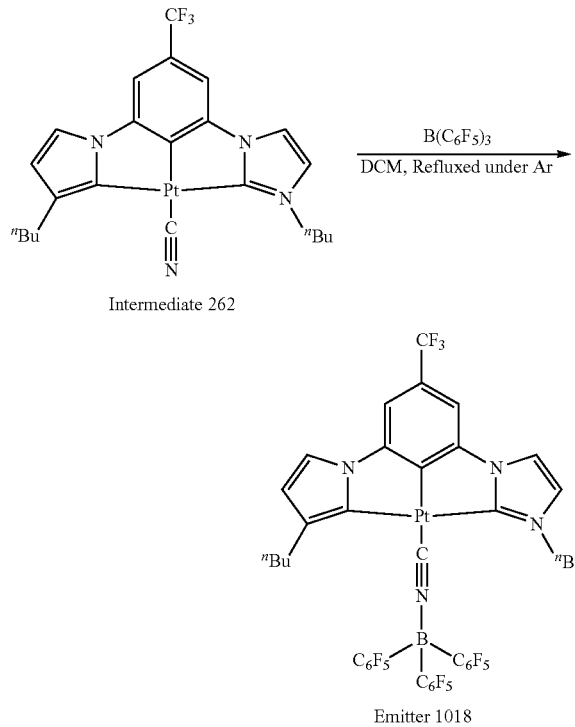

Emitter 1018

The mixture of Intermediate 262 and B(C$_6$F$_6$)$_3$ was pump-filled three times in a flask. Dry dichloromethane was added into the flask. The solution was stirred overnight at room temperature under argon. A solid was obtained after solvent was removed by vacuum. $^1$H NMR (400 MHz, CDCl$_3$): δ=7.45 (s, 2H), 7.45 (t, J=5.36 Hz, 2H), 7.04 (s, 2H), 4.18 (t, J=6.36 Hz, 4H), 1.54 (quint, J=6.80 Hz), 1.04 (next, J=7.68 Hz, 2H), 0.79 (t, J=7.40 Hz, 6H).

Example 311—X-Ray Diffraction Data of Emitter 1016 and Emitter 1017

TABLE 1

Selected bond lengths and angles for complexes

| | | Emitter 1016 | | Emitter 1017 | |
|---|---|---|---|---|---|
| Bond length | Pt1—C1 | 2.033 (4) | Pt1—C1 | 2.044 (7) |
| | Pt1—C4 | 1.990 (4) | Pt1—C4 | 1.982 (7) |
| | Pt1—C12 | 2.050 (4) | Pt1—C10 | 2.050 (7) |
| | Pt1—C39 | 2.016 (4) | Pt1—C21 | 1.998 (7) |
| | C39—N5 | 1.145 (6) | N5—C21 | 1.159 (9) |
| | N5—B1 | 1.584 (6) | N5—B1 | 1.556 (9) |
| Bond angles | C1—Pt1—C4 | 77.58 (16) | C1—Pt1—C4 | 77.7 (3) |
| | C1—Pt1—C12 | 155.17 (16) | C1—Pt1—C10 | 155.4 (3) |
| | C1—Pt1—C39 | 177.21 (15) | C1—Pt1—C21 | 103.5 (3) |
| | C4—Pt1—C12 | 77.90 (16) | C4—Pt1—C10 | 77.7 (3) |
| | C4—Pt1—C39 | 177.21 (15) | C4—Pt1—C21 | 178.0 (3) |

FIG. 11 illustrates a perspective view of Emitter 1016.
FIG. 12 illustrates a perspective view of Emitter 1017.

TABLE 2

Example 312 - Photophysical data for Emitter 1016, Emitter 1017 and Emitter 1018

| | | Emission | | | |
|---|---|---|---|---|---|
| Emitter | UV-vis absorption[a] λ$_{max}$ [nm] (ε [M$^{-1}$ cm$^{-1}$]) | Solution,[a],[c],[d] λ$_{max}$ [nm] (Φ; τ[μs]) | Solid (298 K) λ$_{max}$ [nm] (Φ; τ [μs]) | Thin film[e] λ$_{max}$ [nm] (Φ; τ[μs]) | Glassy (77 K)[f] λ$_{max}$ [nm] (τ [μs]) |
| 1016 | 260 (sh, 38400), 267 (48100) 297 (sh, 8870), 329 (sh, 4760), 357 (8270), 373 (sh, 5180) [417 (br, 89), 442 (br, 48)][b] | 449, 478, 507 (sh), 549 (0.18; 2.0) | 452, 480, 512 (sh), 580 (0.46; 2.33) | 447, 477, 505 (sh) (0.78, 6.6) | 442, 470, 502 (sh) (8.1) |
| 1017 | 260 (sh, 36800), 266 (42600), 293 (sh, 7250), 328 (sh, 3850), 355 (6620), 374 (sh, 3740) [418 (br, 68), 442 (br, 34)][b] | 450, 480, 509 (sh) (0.13; 1.6) | 455, 479, 513 (sh) (0.56; 3.2) | 450, 478, 507 (sh) (0.80; 7.9) | 446, 475, 508 (sh), 548 (10.2) |
| 1018 | 257 (sh, 25424), 266 (33599), 327 (3798), 352 (br, 5740), 372 (sh, 4185) | 443, 472, 502 (sh) (0.07; 0.55) | | | |

[a]Measured in degassed dichloromethane (2 × 10$^{-5}$M) at 298 K unless specified.
[b]Measured in dichloromethane at 1 × 10$^{-3}$M.
[c]Emission quantum yields were determined using quinine sulfate in degassed sulfuric acid as standard (Φ$_r$ = 0.546).
[d]τ = room temperature lifetime.
[e]Measured in PMMA with 5 wt. % complex
[f]Measured in glassy solutions (MeOH/EtOH = 1:4).

Example 313—OLED Fabrication Procedures

In this example, an OLED is fabricated using the following materials: PEDOT:PSS [poly(3,4-ethylenedioxythiophene):poly(styrene sulfonic acid)] (Clevios P Al 4083) that was purchased from Heraeus, and PYD2, DPEPO and TPBi purchased from Luminescence Technology Corp. Each of these materials was used without modification. All Pt(II) emitters were purified by gradient sublimation before use.

In order to fabricate the OLED, the substrate is first cleaned. In this example, glass slides with pre-patterned ITO electrodes used as substrates of OLEDs were cleaned in an ultrasonic bath of Decon 90 detergent and deionized water, rinsed with deionized water, and then cleaned in sequential ultrasonic baths of deionized water, acetone, and isopropanol, and subsequently dried in an oven for 1 hour.

Thereafter, the OLED can be fabricated and characterized. In certain embodiments, the OLED includes one or more emissive layers. An emissive layer can comprise at least one host material and at least one dopant material. The host material provides a base that the dopant coats during fabrication. First, PEDOT:PSS were spin-coated onto the cleaned ITO-coated glass substrate and baked at 120° C. for 20 minutes to remove the residual water solvent in a clean room. Then, blends of PYD2: Pt(II) complex were spin-coated from chlorobenzene atop the PEDOT:PSS layer inside a $N_2$-filled glove box. The thickness for all EMLs was approximately 60 nm. Afterwards, all devices were annealed at 110° C. for 10 min inside the glove box and subsequently transferred into a Kurt J. Lesker SPECTROS vacuum deposition system without exposing to air. Finally, DPEPO (10 nm), TPBi (40 nm), LiF (1.2 nm), and Al (150 nm) were deposited in sequence by thermal evaporation at a pressure of $10^{-8}$ mbar. Electroluminescence (EL) spectra were recorded by an Ocean Optics Maya 2000 pro spectrometer. Luminance, CIE coordination, and CRI were measured by a Photo Research Inc PR-655. Voltage-current characteristics were measured by a Keithley 2400 source-meter measurement unit. All devices were characterized at room temperature without encapsulation. External quantum efficiency (EQE) and power efficiency were calculated by assuming a Lambertian distribution.

TABLE 3

Example 314 - Key performance of OLEDs fabricated from Emitter 1016, Emitter 1017, Emitter 1018 and a model complex for comparison.

| Device | Complex (wt %) | CE[a] (cd A$^{-1}$) | EQE[b] (%) | CIE[c] (x, y) |
|---|---|---|---|---|
| 401 | model (4%) | 2.79 | 1.30 | (0.20, 0.33) |
| 402 | model (10%) | 7.20 | 3.07 | (0.23, 0.35) |
| 403 | 1016 (4%) | 14.28 | 6.97 | (0.18, 0.30) |
| 404 | 1016 (10%) | 19.79 | 8.84 | (0.20, 0.33) |
| 405 | 1017 (4%) | 32.19 | 14.66 | (0.17, 0.32) |
| 406 | 1017 (10%) | 24.70 | 11.41 | (0.16, 0.32) |
| 407 | 1018 (4%) | 6.16 | 4.10 | (0.16, 0.20) |
| 408 | 1018 (12%) | 13.77 | 8.64 | (0.15, 0.21) |

[a]Maximum power efficiency.
[b]Maximum external quantum efficiency.
[c]CIE coordinates at 100 cd m$^{-2}$.

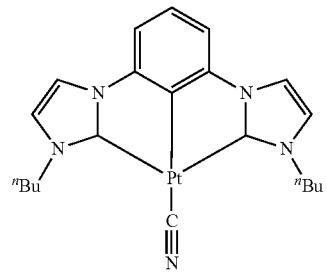

Chemical structure of model complex

FIG. 13 provides a graphical representation of the comparison of solution PL and EL spectra of the model complex. FIGS. 14-16 provide graphical representations of the comparison of solution PL and EL spectra of Emitter 1016, Emitter 1017, and Emitter 1018, respectively.

Like the cases in other [Pt(II)C(NHC)^C^C(NHC)] complexes, excimer emission arises in devices 401 and 402, which make the emission color red-shifted.

However, when the ESG is added, the EL spectra of devices 403-408 are at the same range of the corresponding PL spectra. Excimer emission is successfully suppressed. Therefore, blue OLED can be obtained with this system.

Besides the emission color, the device efficiencies of devices 403-408 are much higher than the device fabricated by model complex.

Example 315—OLED Performance for Emitter 1017 with Modified Device Structure

The modified device structure is: ITO/NPB (30 nm)/mCP (10 nm)/BOCP: Emitter 1017(30 nm)/PhOXD (40 nm)/LiF (1.2 nm)/Al (150 nm). All layers in this device are fabricated by vacuum deposition.

| Concentration (wt %) | Max. CE (cd A$^{-1}$) | Max. EQE (%) | CIE (x, y) |
|---|---|---|---|
| 3 | 20.70 | 13.04 | 0.15, 0.21 |
| 8 | 27.54 | 16.58 | 0.15, 0.22 |
| 15 | 13.86 | 7.88 | 0.16, 0.23 |

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:
1. A blue organic light-emitting diode (OLED) emitter having a chemical structure according to Structure I:

Structure I

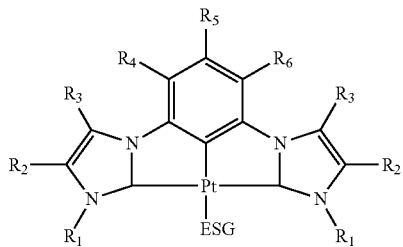

wherein
$R_1$-$R_6$ are independently selected from hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;
each pair of adjacent R groups of $R_1$-$R_6$ forms 5-8 member ring(s) with other carbon or nitrogen atoms;
ESG is an excimer emission suppression group; and
wherein the emitter has an emission wavelength between 440 nm and 500 nm.

2. The OLED emitter of claim 1, wherein $R_1$-$R_6$ is independently selected from hydrogen, halogen, hydroxyl, an unsubstituted alkyl containing from 1 to 20 carbon atoms, a substituted alkyl containing from 1 to 20 carbon atoms, cycloalkyl containing from 4 to 20 carbon atoms, an unsubstituted aryl containing from 6 to 20 carbon atoms, a substituted aryl containing from 6 to 20 carbon atoms, acyl containing from 1 to 20 carbon atoms, alkoxy containing from 1 to 20 carbon atoms, acyloxy containing from 1 to 20 carbon atoms, amino, nitro, acylamino containing from 1 to 20 carbon atoms, aralkyl containing from 1 to 20 carbon atoms, cyano, carboxyl containing from 1 to 20 carbon atoms, thiol, styryl, aminocarbonyl containing from 1 to 20 carbon atoms, carbamoyl containing from 1 to 20 carbon atoms, aryloxycarbonyl containing from 1 to 20 carbon atoms, phenoxycarbonyl containing from 1 to 20 carbon atoms, or an alkoxycarbonyl group containing from 1 to 20 carbon atoms.

3. The OLED emitter of claim 1, wherein the ESG group is

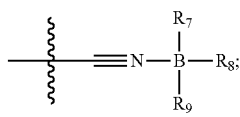

and $R_7$-$R_9$ are independently an unsubstituted alkyl, a substituted alkyl, cycloalkyl, an unsubstituted aryl, a substituted aryl, acyl, alkoxy, acyloxy or amino group.

4. The OLED emitter of claim 1, wherein ESG is:

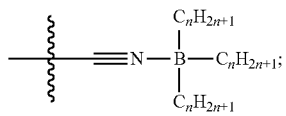

and n is an integer.

5. The OLED emitter of claim 1, wherein ESG is:

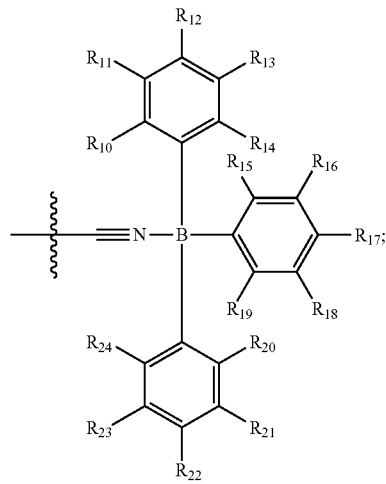

and $R_{10}$-$R_{24}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group.

6. The OLED emitter of claim 1, wherein ESG is:

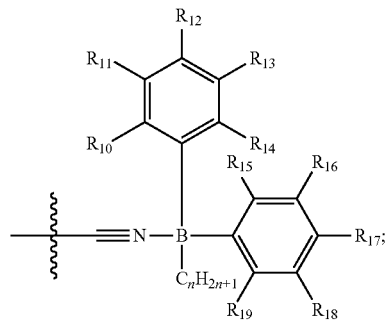

$R_{10}$-$R_{19}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group; and n is an integer.

7. The OLED emitter of claim 1, wherein ESG is:

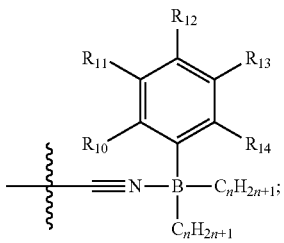

$R_{10}$-$R_{14}$ are independently hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group; and n is an integer.

8. The OLED emitter of claim 1, wherein the ESG is selected to produce an $\lambda_{max}$ emission having a red-shift of less than 10 nm as compared with an OLED emitter having a halogen in place of the ESG.

9. The OLED emitter of claim 1, wherein the OLED emitter produces no excimer emission in an EL spectrum.

10. The OLED emitter of claim 1, wherein the OLED emitter produces an emission $\lambda_{max}$ in an EL spectrum that is less than an emission $\lambda_{max}$ produced in a solution PL spectrum.

11. The OLED emitter of claim 1, wherein the OLED emitter produces an EL spectrum that approximates a solution PL spectrum having no excimer emission produced by the OLED emitter.

12. The OLED emitter of claim 1, wherein the OLED emitter produces a blue emission having a CIE chromaticity x-coordinate of less than 0.20.

13. The OLED emitter of claim 1, wherein the OLED emitter produces a blue emission having a CIE chromaticity y-component of less than 0.35.

14. The OLED emitter of claim 1, wherein the OLED emitter produces a blue emission having an emission $\lambda_{max}$ of less than 500 nm in a solution.

15. The OLED emitter of claim 1, wherein the OLED emitter produces an excimer emission lifetime of less than 10 μs.

16. The OLED emitter of claim 1, wherein the OLED emitter is selected from the group of Emitter 1001, Emitter 1002, Emitter 1003, Emitter 1004, Emitter 1005, Emitter 1006, Emitter 1006, Emitter 1007, and Emitter 1018, the group having chemical structures of:

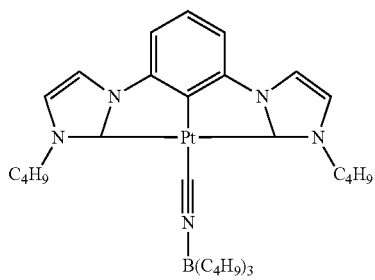

Emitter 1001

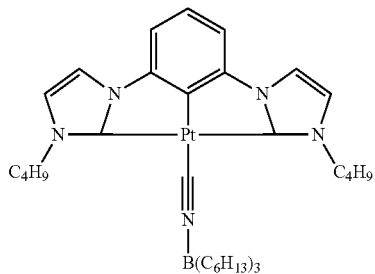

Emitter 1002

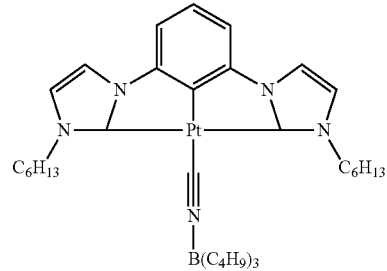

Emitter 1003

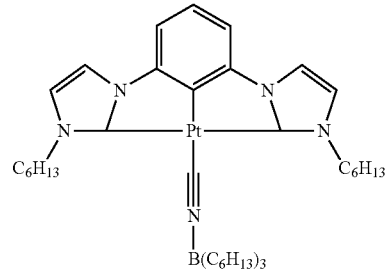

Emitter 1004

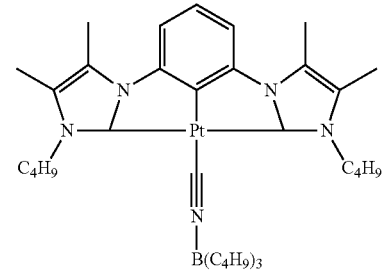

Emitter 1005

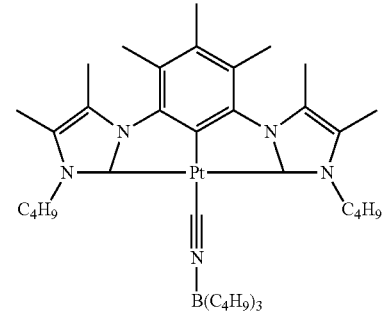

Emitter 1006

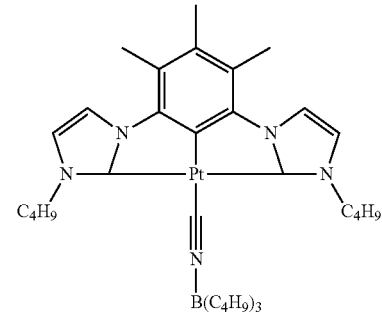

Emitter 1007

Emitter 1008
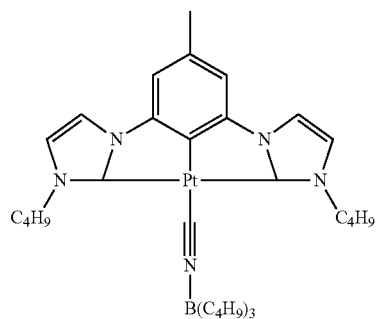
Emitter 1009
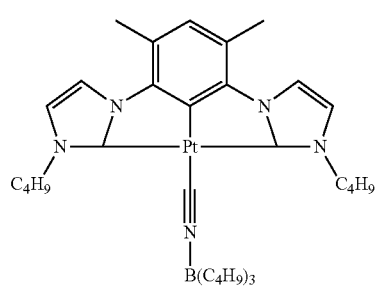
Emitter 1010
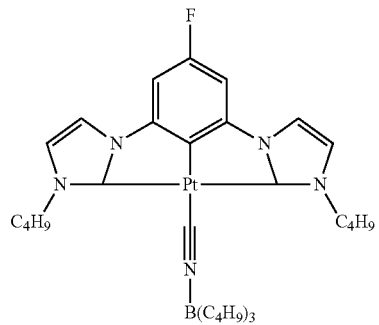
Emitter 1011
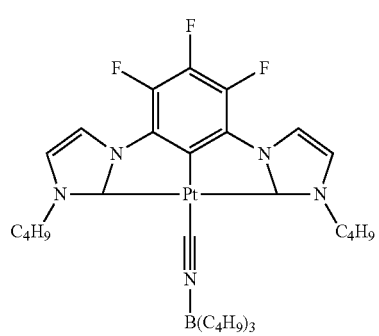
Emitter 1012
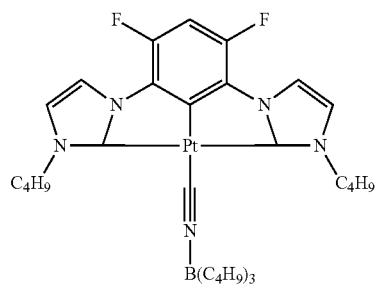
Emitter 1013
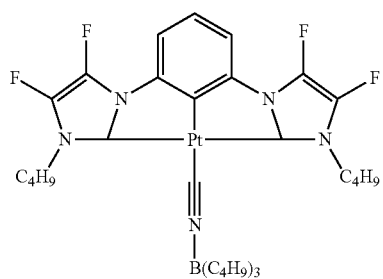
Emitter 1014
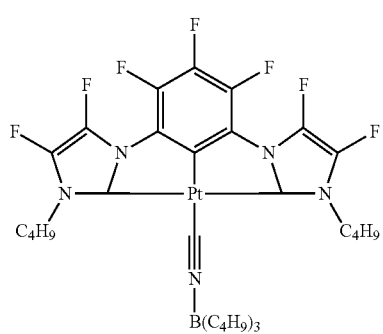
Emitter 1015
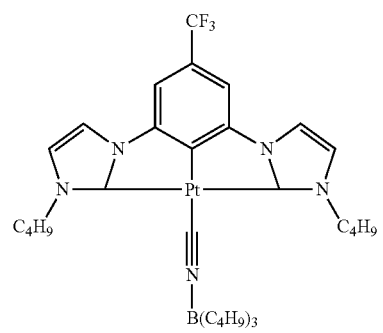
Emitter 1016
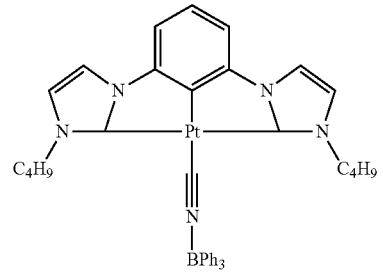
Emitter 1017
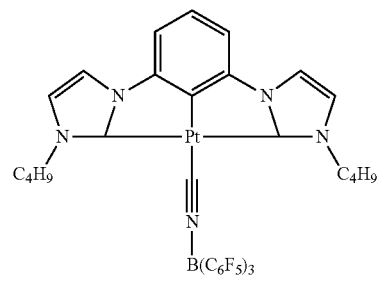

-continued

Emitter 1018

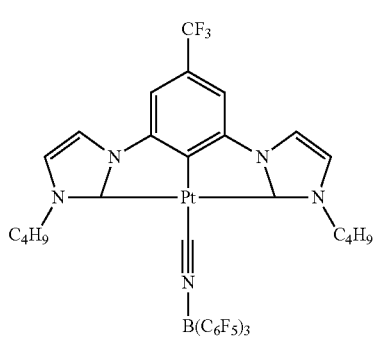

17. A light-emitting device, comprising:
at least one OLED emitter as an emitting material, wherein the OLED emitter has a chemical structure according to Structure I:

Structure I

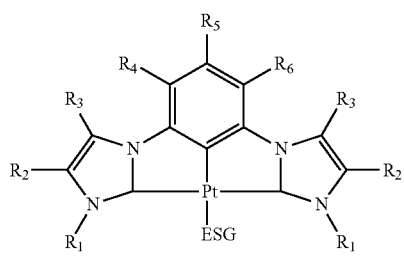

and wherein
  $R_1$-$R_6$ are independently selected from hydrogen, halogen, hydroxyl, an unsubstituted alkyl, a substituted alkyl, cycloalkyl, an unsubstituted aryl, a substituted aryl, acyl, alkoxy, acyloxy, amino, nitro, acylamino, aralkyl, cyano, carboxyl, thio, styryl, aminocarbonyl, carbamoyl, aryloxycarbonyl, phenoxycarbonyl, or an alkoxycarbonyl group;
  each pair of adjacent R groups of $R_1$-$R_6$ forms 5-8 member ring(s) with other carbon or nitrogen atoms;
  ESG is an excimer emission suppression group; and
  wherein the emitter has an emission wavelength maximum between 440 nm and 500 nm.

18. The light-emitting device of claim 17, wherein the light-emitting device is an organic light-emitting diode (OLED).

19. The device of claim 17, wherein the device is fabricated by vacuum deposition.

20. The device of claim 17, wherein the device is fabricated by solution processes.

21. The device of claim 17, wherein the dopant concentration is greater than 5 percent by weight.

22. The device of claim 17, wherein the device contains an emissive layer comprising at least one host material and one dopant material.

23. The device of claim 17, wherein the device contains a plurality of emissive layers and each emissive layer comprises at least one host material and one dopant material.

24. A method of making the OLED emitter of claim 1, comprising the steps of:
  (i): reacting, in the presence of CuO and a metal carbonate in a first solvent, a first raw material having a structure of

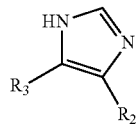

with a second raw material having a structure of

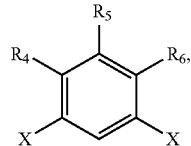

wherein X is a halogen atom, to produce a first intermediate having a structure of

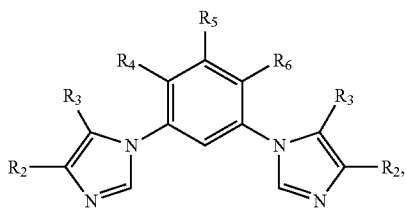

(ii): reacting, in a second solvent, the first intermediate in the presence of $R_1$—X to produce a second intermediate having a structure of

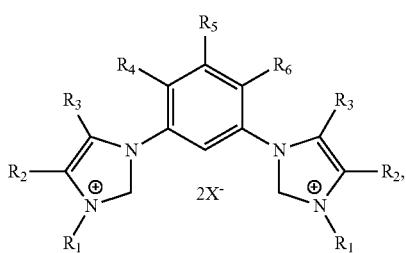

(iii): reacting, in a third solvent, the second intermediate with a platinum salt, to produce a third intermediate having a structure of

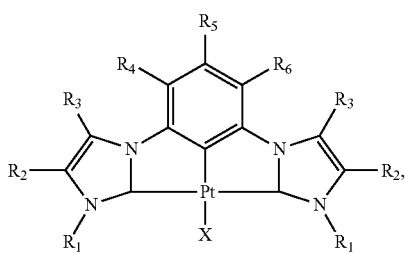

(iv): reacting, in a fourth solvent, the third intermediate with a cyanide salt to produce a fourth intermediate, and
  (v): reacting the fourth intermediate with a compound containing boron to produce the OLED emitter of claim 1.

25. The method of claim 24, wherein the first, second, third, and fourth solvents are the same.

26. The method of claim 24, wherein the first, second, third, and fourth solvents are different.

27. The method of claim 24, wherein the reacting steps are performed in the presence of heat.

28. The method of claim 24, wherein the first raw material is a substituted imidazole.

29. The method of claim 24, wherein the first raw material is an unsubstituted imidazole.

30. The method of claim 24, wherein the second raw material is a substituted benzene.

* * * * *